(12) United States Patent
Oh et al.

(10) Patent No.: US 7,511,034 B2
(45) Date of Patent: Mar. 31, 2009

(54) DIALKYLHYDROXYBENZOIC ACID DERIVATIVES CONTAINING METAL CHELATING GROUPS AND THEIR THERAPEUTIC USES

(75) Inventors: Eu-Gene Oh, Taejon (KR); Sung-Bo Ko, Taejon (KR); Kyung-Hwa Kim, Taejon (KR); In-Kyu Chang, Taejon (KR); Dennis W. Choi, St. Louis, MO (US); Laura L. Dugan, St. Louis, MO (US); Jae-Young Koh, Seoul (KR); In-Jae Shin, Koyang (KR); Moo-Ho Won, Chuncheon (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 11/329,926

(22) Filed: Jan. 11, 2006

(65) Prior Publication Data

US 2006/0116377 A1   Jun. 1, 2006

Related U.S. Application Data

(63) Continuation of application No. 10/456,399, filed on Jun. 5, 2003, now Pat. No. 7,229,988, which is a continuation of application No. PCT/KR01/01273, filed on Jul. 26, 2001.

(51) Int. Cl.
*A61K 31/54* (2006.01)
*A61K 31/35* (2006.01)
*C07D 279/00* (2006.01)
*C07D 277/04* (2006.01)
*C07D 207/46* (2006.01)

(52) U.S. Cl. ............ 514/222.2; 514/228.8; 514/252; 514/256; 514/277; 514/364; 514/365; 514/372; 514/378; 514/399; 514/406; 514/427; 514/432; 514/457; 544/6; 544/66; 544/98; 548/146; 548/214; 548/215; 548/252; 548/260; 548/303.1; 548/336; 548/337; 548/373.1; 548/570

(58) Field of Classification Search ............... 544/8, 544/66, 98, 215, 328, 336, 497; 548/146, 548/214, 215, 252, 260, 303.1, 336, 337, 548/373.1, 570; 549/98, 192, 197; 562/473; 514/222.2, 228.8, 252, 256, 277, 364, 365, 514/372, 378, 399, 406, 427, 432, 457
See application file for complete search history.

(56) References Cited

U.S. PATENT DOCUMENTS 2,401,522 A   6/1946   Stoll et al.

(Continued)

FOREIGN PATENT DOCUMENTS

| JP | 2002372625 | 12/2002 |
|---|---|---|
| WO | WO98/08831 | 3/1998 |

OTHER PUBLICATIONS

Moffett et al, Jol. Med. Pharm. Chem. vol. 2 No. 2 pp. 201-212 (1980).*

(Continued)

*Primary Examiner*—Janet L. Andres
*Assistant Examiner*—Raymond Covington
(74) *Attorney, Agent, or Firm*—Knobbe Martens Olson & Bear LLP

(57) ABSTRACT

Novel dialkylhydroxybenzoic acid derivatives containing metal chelating groups are disclosed. The novel compounds are used as therapeutics for treating and/or preventing various medical dysfunctions and diseases arising from reactive oxygen species and/or excess Zn ions, in particular stroke, Parkinson's disease, Alzheimer's disease. The compounds have not only low toxicity but also similar or superior LPO inhibition activity to references. They also effectively inhibit the cerebral neuronal cell death by ROS and/or zinc ion, and show neuroprotective effects against ischemic neuronal degeneration.

14 Claims, 13 Drawing Sheets

U.S. PATENT DOCUMENTS

| | | | |
|---|---|---|---|
| 4,052,361 | A | 10/1977 | Susi et al. |
| 4,908,363 | A | 3/1990 | Klötzer et al. |
| 5,008,394 | A | 4/1991 | Günther et al. |
| 5,510,478 | A | 4/1996 | Sabb |
| 5,827,880 | A | 10/1998 | Malroy-Camine et al. |

OTHER PUBLICATIONS

Chem. Abs 78813 vol. 72, 1970, Keil et al , Antimicrob. Agents Chemo. vol. 1969 pp. 120-127 (1970). Best availble.*

McGraw-Hill Dictionary of Chemical Terms(1990) pp. 282.*

Concise Encyclopedia Chemistry (1993) pp. 490.*

Hawlev's Condensed Chemical Dictionary (1993) pp. 594.*

Aksenova et al., "Aging in a dish: Age-dependent changes of neuronal survival, protein oxidation, and creatine kinase BB expression in long-term long-term hippocampal cell culture," Journal of Neuroscience Research, 1999, pp. 308-317, vol. 58.

Boldyrev et al., "Protection of neuronal cells against reactive oxygen species of carnosine and related compounds," Comparative Biochemistry and Physiology Part B, 2004, pp. 81-88, vol. 137.

Mandel et al., "Proceedings frome the "Third International Conference on Mechanism of Action of Nutraceuticals,"" Journal of Nutritional Biochemistry, 2005, pp. 513-520, vol. 16.

Parnetti, L. et al., Cognitive Enhancement Therapy for Alzheimer's Disease, Drugs, 53:752-768 (1997).

Grisar J. M. et al., 2,3-Dihydro-1-benzofuran-5-ols as Analogues of α-Tocopherol That Inhibit in Vitro and ex Vivo Lipid Autoxidation and Protect Mice against Central Nervous System Trauma, J. Med. Chem., 38:453-458(1995).

Thomas G. Back and Brian P. Dyck, A Novel Camphor-Derived Selenenamide That Acts as a Glutathione Peroxidase Mimetic, J. Am. Chem. Soc., 119:2079-0283 (1997).

Sies, et al., Ebselen as a Glutathione Peroxidase Mimic and as a Scavenger of Peroxynitrite, Adv. Pharmaco., 38:229-246 (1997).

Koh, et al., The Role of Zinc in Selective Neuronal Death after Transient Global Gerebral Ischemia, Science, vol. 272, 1013-1016 (1996).

Kim, et al., Zinc-Induced Cortical Neuronal Death with Features of Apoptosis and Necrosis: Mediation by Free Radicals, Neuroscience, 89:175-182 (1999).

Bray et al, Chemical Abstract, vol. 42, No. 2961, Fate of Certain Organic Acids and Amides in the Rabbit:, (1947).

Ashley I. Bush, The Metallobiology of Alzheimer's disease, Elsevier, Trends in Neurosciences vol. 26, No. 4, Apr. 2003, pp. 207-214.

Ashley I Bush, Metal complexing agents as therapies for Alzheimer's disease, Elsevier, Neurobiology of Aging, vol. 23, 2002, pp. 1031-1038.

* cited by examiner

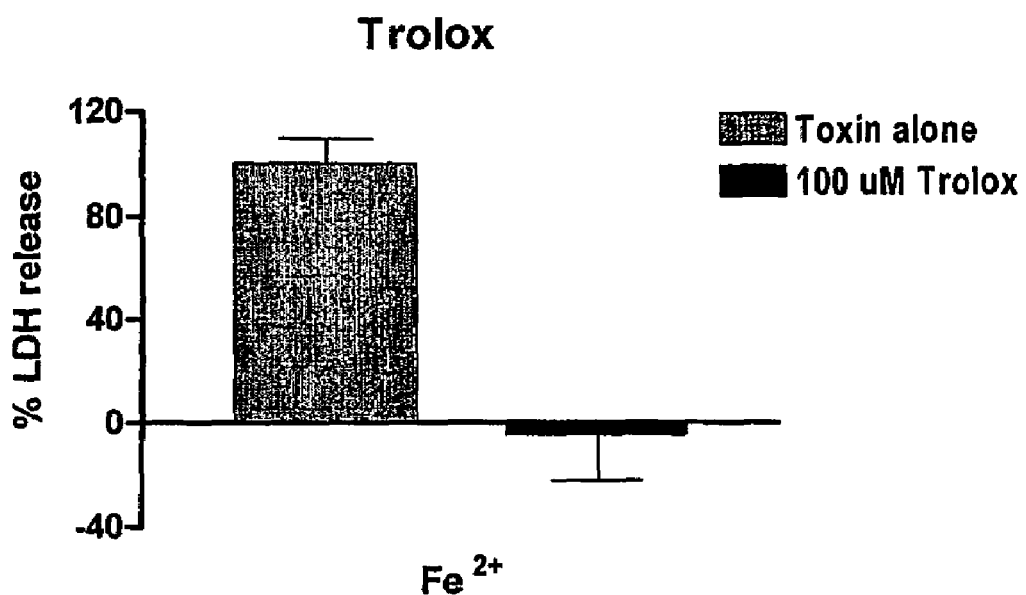
Fig. 1-a
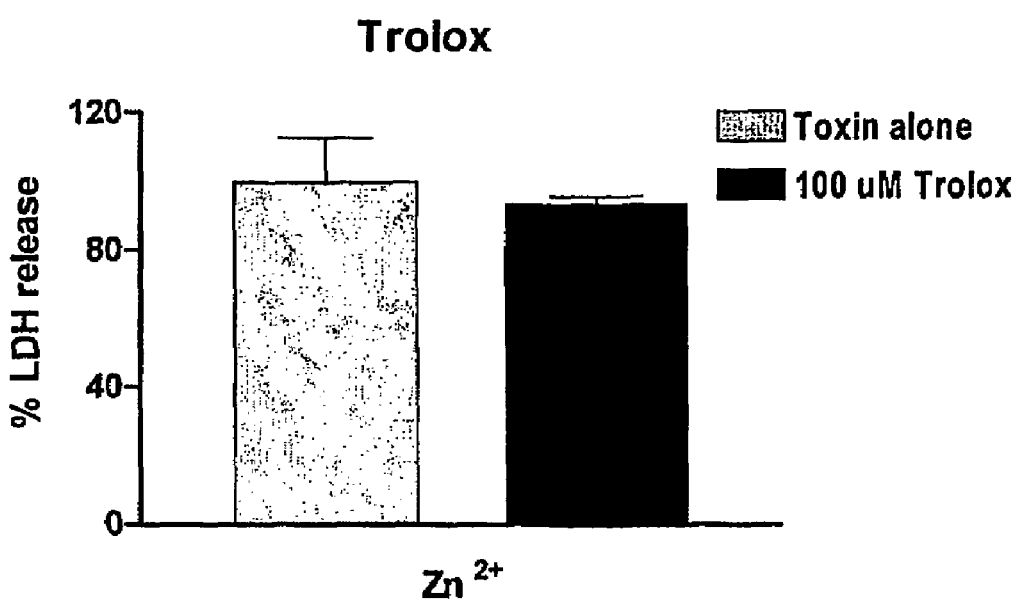
Fig. 1-b

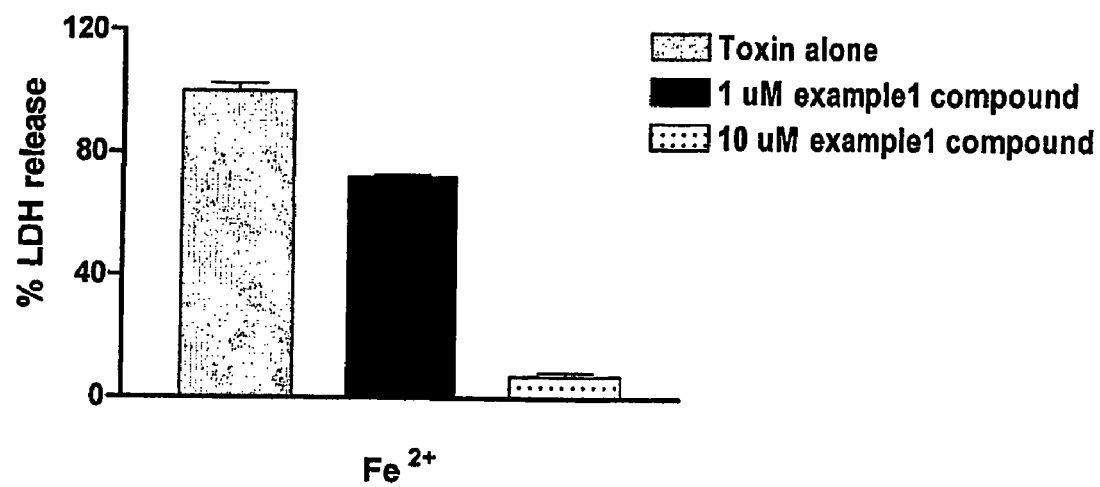
Fig. 2-a
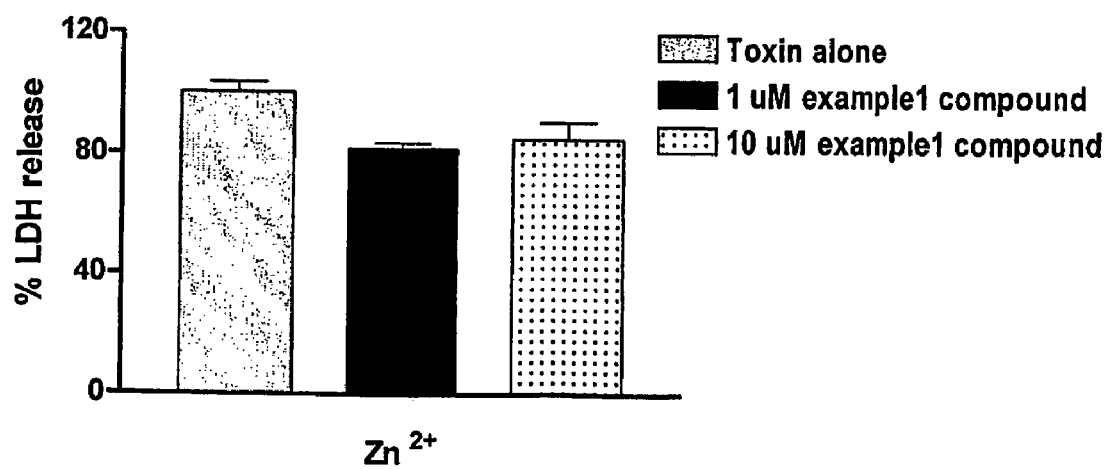
Fig. 2-b

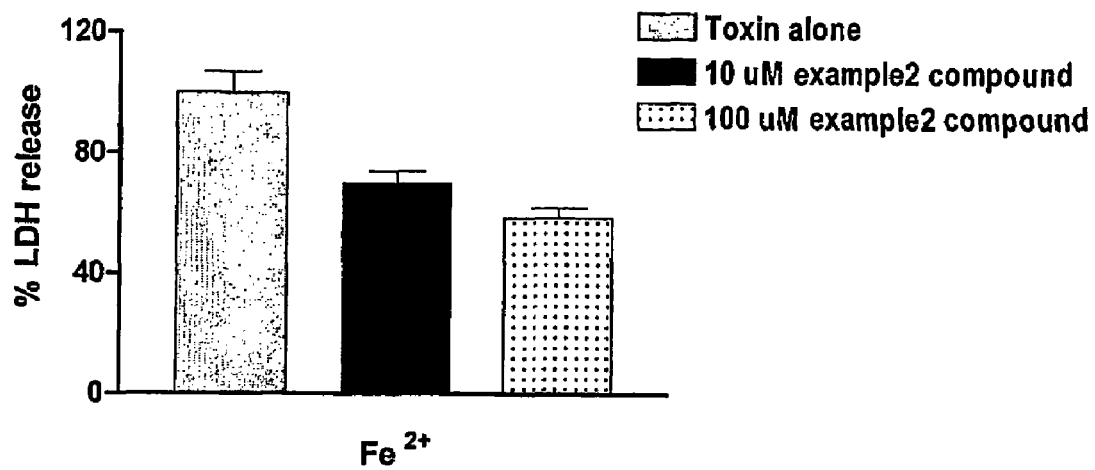
Fig. 3-a
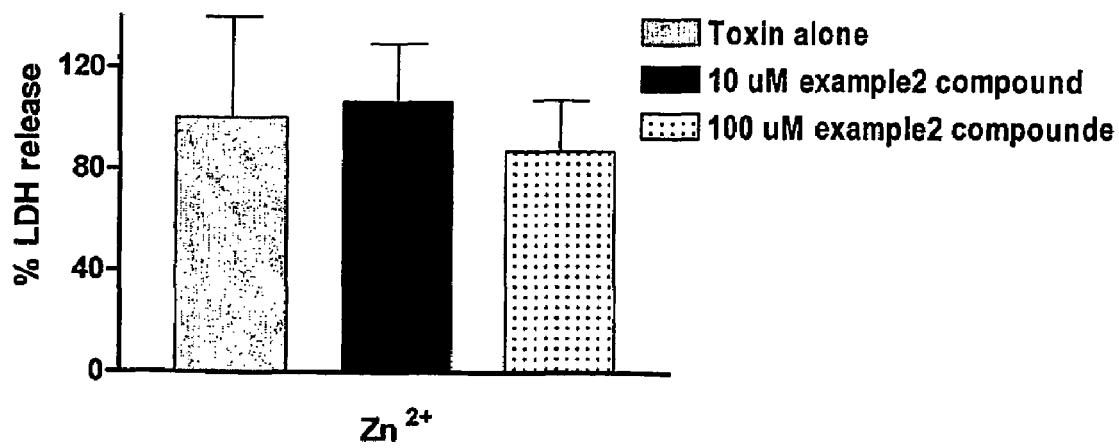
Fig. 3-b

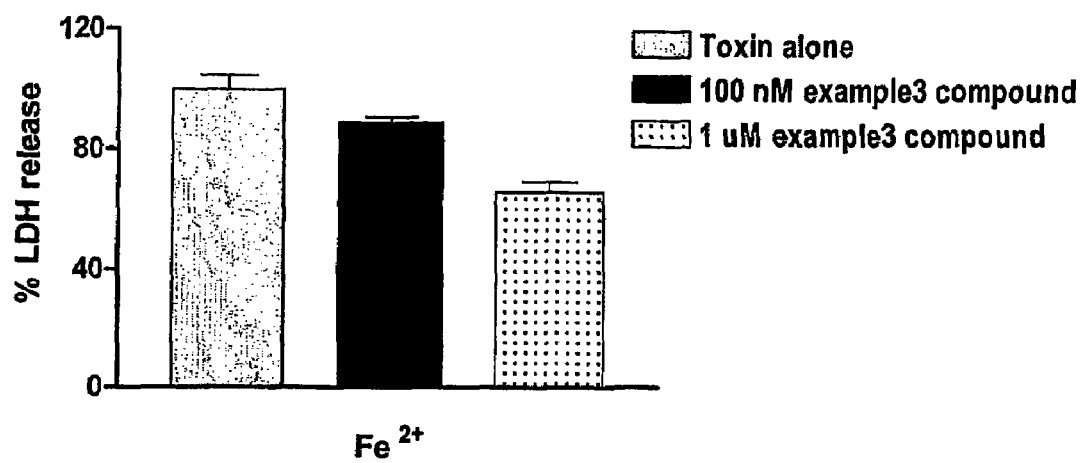
Fig. 4-a
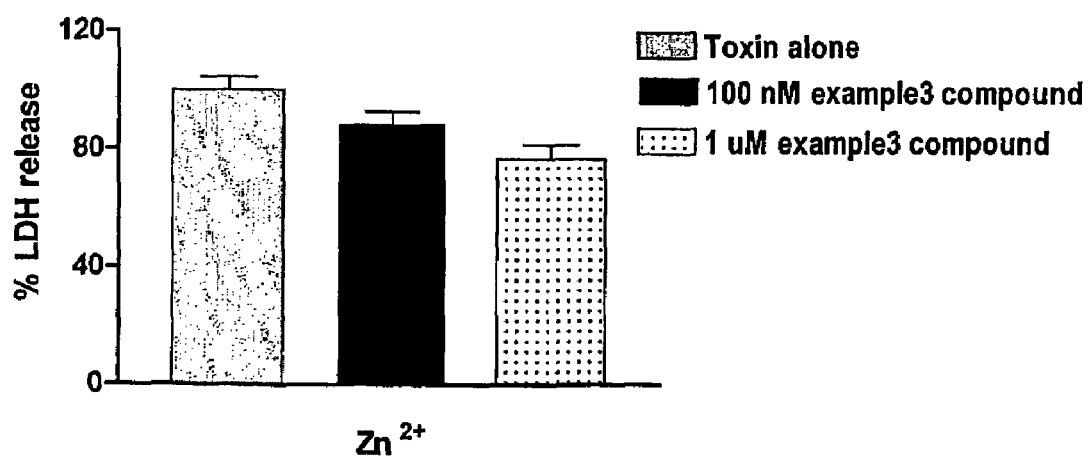
Fig. 4-b

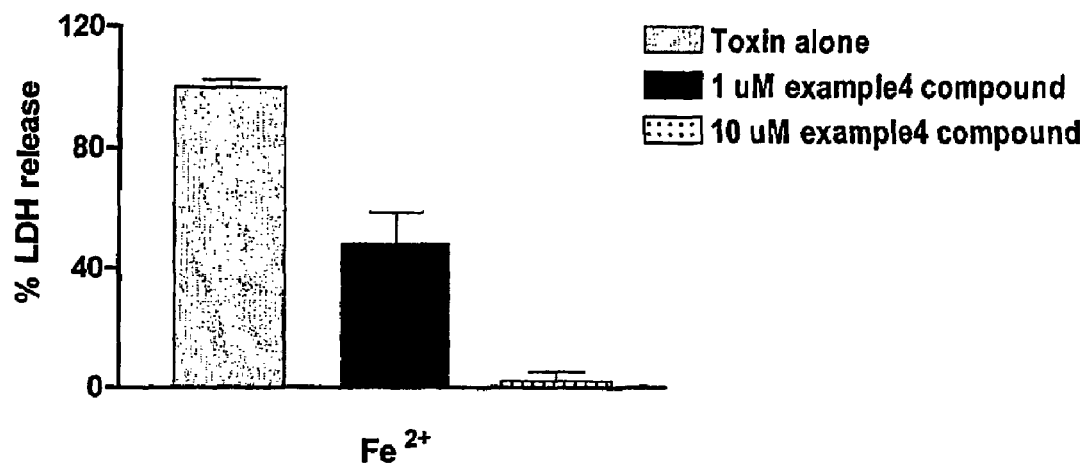
Fig. 5-a
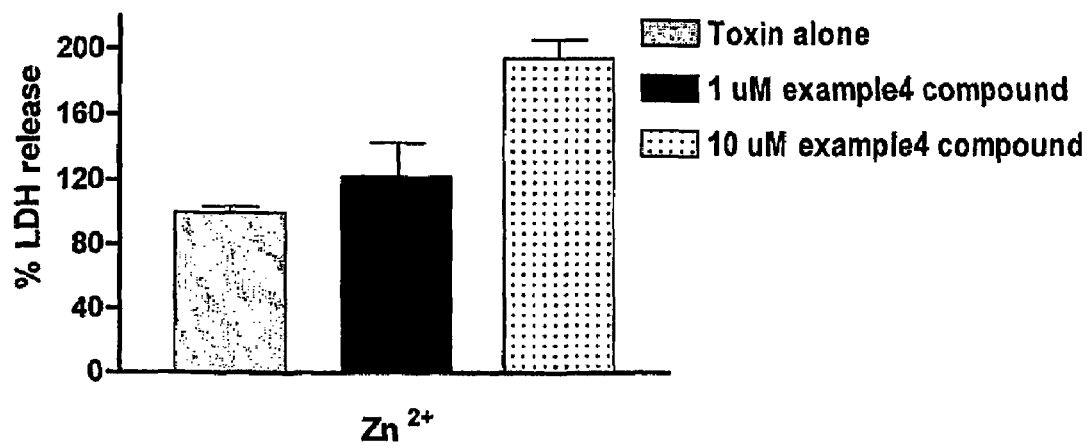
Fig. 5-b

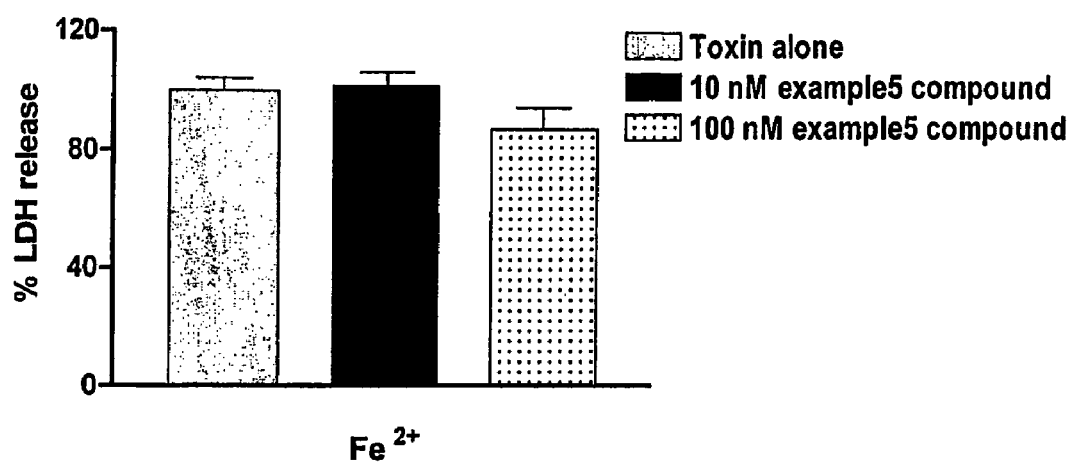
Fig. 6-a
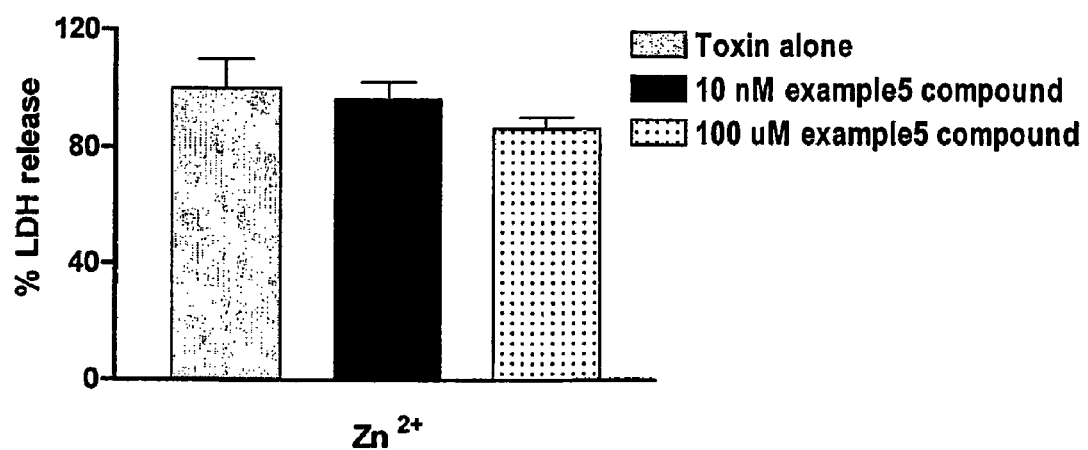
Fig. 6-b

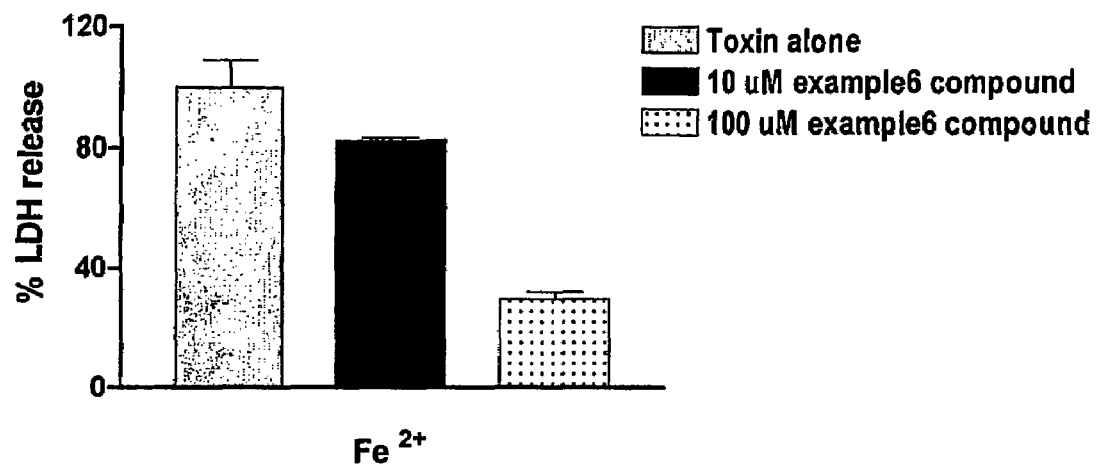
Fig. 7-a
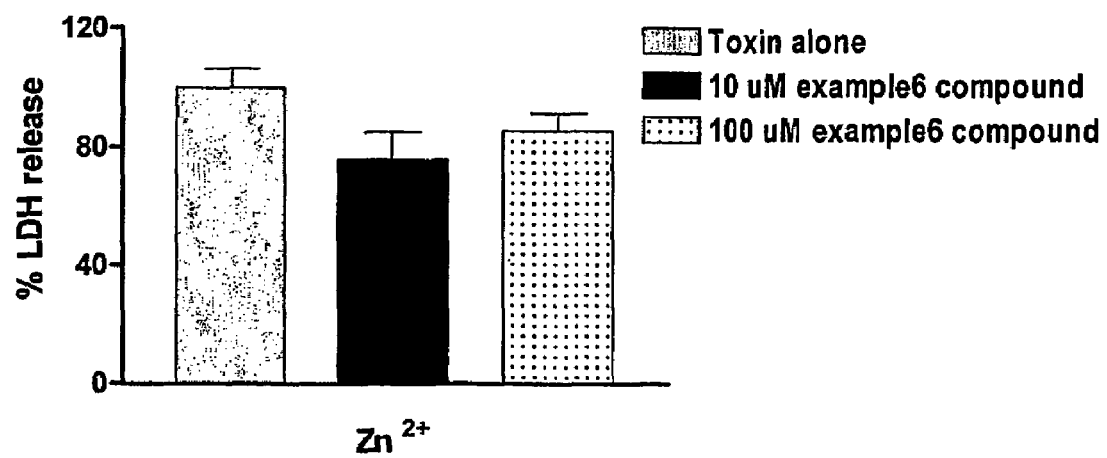
Fig. 7-b

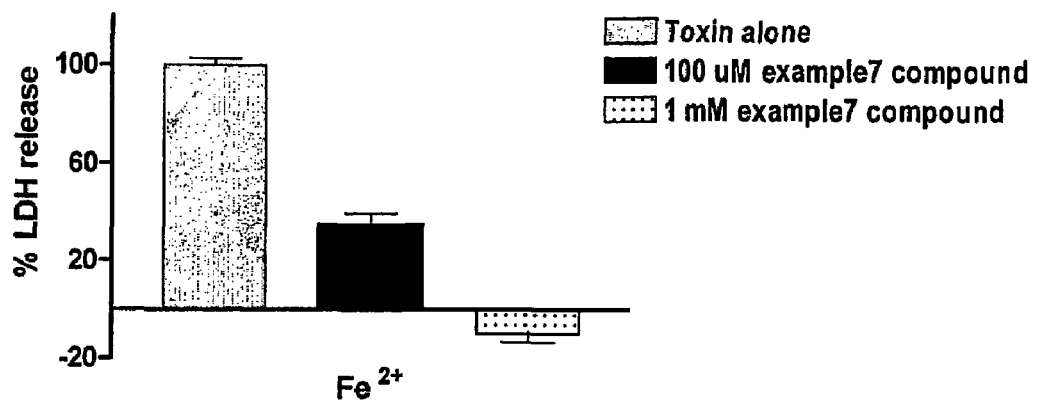
Fig. 8-a
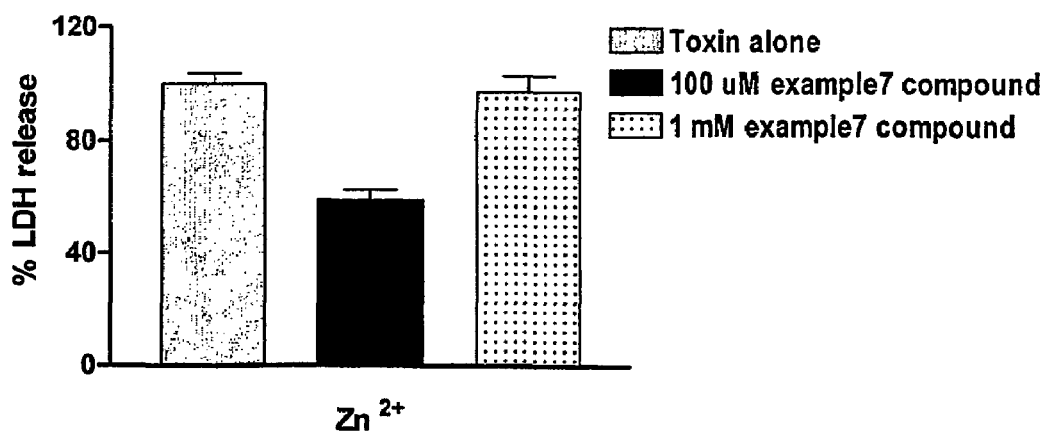
Fig. 8-b

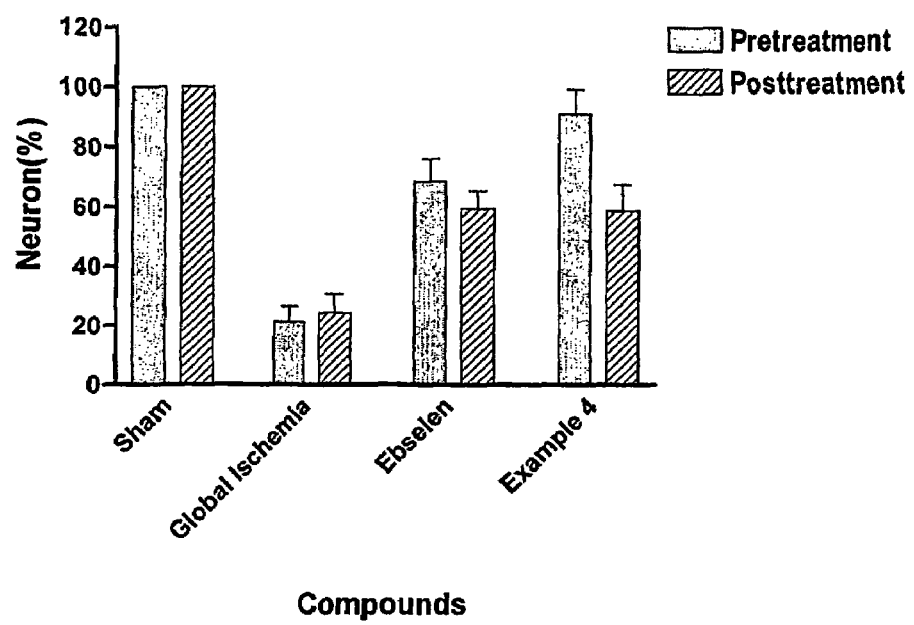
Fig. 17-a
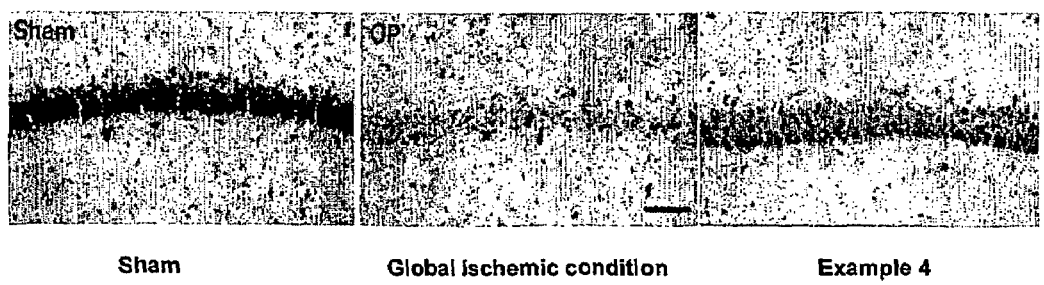
Fig. 17-b

DIALKYLHYDROXYBENZOIC ACID DERIVATIVES CONTAINING METAL CHELATING GROUPS AND THEIR THERAPEUTIC USES

CROSS-REFERENCE OF RELATED APPLICATIONS

This application is a continuation of U.S. patent application Ser. No. 10/456,399, filed Jun. 5, 2003 now U.S. Pat. No. 7,229,988, now pending, which is a continuation under 35 U.S.C. § 365 (c) claiming the benefit of the filing date of International Patent Application No. PCT/KR01/01273 designating the United States, filed Jul. 26, 2001. The PCT Application was published in English as WO 03/010143 A1 on Feb. 6, 2003. The contents of U.S. patent application Ser. No. 10/456,399 and International Patent Application No. PCT/KR01/01273 are incorporated herein by reference in their entirety.

BACKGROUND OF THE INVENTION

1. Field of the Invention

The present invention relates to novel dialkylhydroxybenzoic acid derivatives containing metal chelating groups, and pharmaceutical compositions containing the novel compounds as active ingredients, more particularly, to novel dialkylhydroxybenzoic acid derivatives containing metal chelating groups, and to the use of the novel compounds as therapeutics for treating and/or preventing various medical dysfunctions and diseases caused by reactive oxygen species and/or excess Zn ions, in particular stroke, Parkinson's disease, and Alzheimer's disease.

2. Description of the Related Technology

According to Harman's free-radical theory of ageing, successive oxidation attacks create "oxidative stress" conditions, that is, create an imbalance between the protective systems in favour of the pro-oxidants. Such attacks result in numerous molecular modifications, especially of polyunsaturated membrane lipids, proteins and nucleic acids. Human and animal organisms possess various defense mechanisms that act in synergy. Those mechanisms are of an enzymatic nature (superoxide dismutase, catalase, and glutathione peroxidase) or of a non-enzymatic nature (such as vitamins E and C, which enable physiological control of free-radical activity). With ageing, however, that protection becomes less efficient, not to say inefficient, especially as a result of the decreased activity of a large number of enzymes including those involved in such defense mechanisms. Consequently, for some disorders associated with ageing, such as atherosclerosis, cataract, non-insulin-dependent diabetes, cancer or chronic neurodegenerative disorders, numerous studies have been able to demonstrate that such conditions are associated with those "oxidative stress" conditions.

The central nervous system is especially sensitive to "oxidative stress" because of its high oxygen consumption, the relatively low levels of its antioxidant defenses and the high iron concentration of some cerebral regions. This explains why "oxidative stress" might be one of the main etiological factors of cerebral ageing, as well as of acute central nervous system disorder such as stroke, neurodegenerative disorders such as Parkinson's disease, Alzheimer's disease, and neurodegeneracies of the basal ganglia. The rate of occurrence of neurodegenerative disorders of central nervous system increases worldwide. Stroke occupies the third highest cause of death following cardiovascular diseases and malignant tumors (see: Parnetti, L. et al., Drug, 53:752 (1997)).

Antioxidants protecting neuron cell of brain from oxidative stress include vitamin E derivatives such as Trolox (see: J. Med. Chem., 38:453 (1995)), glutathione peroxidase (hereinafter, referred to as "GPx") mimics (see: Daiichi Pharmaceutical Co., Ltd., Annual Report (1999); WO 9808831; U.S. Pat. No. 5,008,394; J. Am. Chem. Soc., 119:2079-2083 (1997); Adv. Pharmacol., 38:229 (1996)), superoxide dismutase (SOD) mimics (see: U.S. Pat. No. 5,827,880), and spin trapping agents (see: J. Med. Chem., 39:4988 (1996); U.S. Pat. No. 5,475,032).

A GPx mimic is synthesized compound mimicking the function of selenocystein from GPx active site. A well-known GPx mimic, Ebselen seems to have no major toxicity in preclinical and clinical tests and it is proposed as a potential drug for stroke. Ebselen is, however, very little soluble in water, even in the presence of an excess of glutathione (GSH), which limits its pharmacological applications.

Spin trapping agents may be developed as an antioxidant if they can trap hazardous free radicals enough, which include $\alpha$-phenyl-N-tert-butylnitrone (PBN), and various derivatives of PBN have been developed. Generally, nitrone moiety increases the solubility of compounds in water. However, it has revealed shortcomings such as a low lipid peroxidation inhibition activity in vitro and a low protection of brain cells in vivo (see: Fevig, Thomas L. et al., J. Med. Chem., 39:4988-4996 (1996)).

On the other hand, zinc ion, which is present with high concentration (>10 mM) in synaptic vesicle storing brain neurotransmitters, is a necessary element in normal function of human cells. As soon as a neuron is stimulated, zinc ion is released into interstitial fluid and then plays a crucial role in signal transmission from neuron to neuron, especially signal transmission by glutamate.

Furthermore, a variety of studies have reported that zinc ion in the synapse may play a central role in the pathological phenomena of central nervous system. The exposure of brain cortex neuron cells to excess zinc results in the immediate neuron cell injury, while the concentration of zinc is similar to that of zinc released from the brain in convulsion or ischemia. Hence, zinc is supposed to evoke neuron cell injury, by way of the influx of excess zinc into neuron cells. In accordance with the above hypothesis, it was found that translocation of synapse zinc in neuron cells was a main cause of selective neuronal cell injury after transient global cerebral ischemia rather than excitotoxicity by calcium (see: Koh, J.-Y et al, Science, 272:1013-1016 (1996); Kim, Y.-H. et al, Neuroscience, 89: 175-182 (1999)). It is more plausible that the neurotoxicity by the translocation of zinc may play a central role in acute neuron cell death derived from focal ischemia. Therefore, the chelation of zinc is supposed to be effective on persisting protection of neuron cells. However, the zinc chelator for the treatment and prevention of neurodegenerative disease of central nervous system is not developed yet.

SUMMARY OF CERTAIN INVENTIVE ASPECTS

The present inventors synthesized novel compounds by introducing metal chelating group into a novel structure of phenolic type antioxidant, a reactive oxygen species (ROS) scavenger, and they found that the said compounds possess a protective activity in cerebral neuron cells against zinc ions, reactive oxygen species (ROS) and neuro-excitotoxic factors, while showing a low toxicity. As a result, the said compounds could be potential drug candidates for the treatment and prevention of cell death of brain cells.

An aspect of the invention provides novel dialkylhydroxy benzoic acid derivatives containing metal chelating groups.

Another aspect of the invention provides pharmaceutical compositions comprising a dialkylhydroxy benzoic acid derivative compound as an active ingredient. The pharmaceutical compositions can be used for the treatment and/or prevention of medical dysfunctions and diseases such as stroke, Parkinson's disease, and Alzheimer's disease caused by reactive oxygen species and/or excess Zn ions.

Another aspect of the invention provides a method for treating a living body in need of protection of neuronal cells from damage caused by a reactive oxygen species or a neuroexcitotoxic factor.

BRIEF DESCRIPTION OF DRAWINGS

The above and the other objects and features of the present invention will become apparent from the following descriptions given in conjunction with the accompanying drawings.

FIG. 1-a is a graph showing the results of combined treatment of Trolox and $Fe^{2+}$ toxin.

FIG. 1-b is a graph showing the results of combined treatment of Trolox and $Zn^{2+}$ toxin.

FIG. 2-a is a graph showing the results of combined treatment of compound obtained in Example 1 and $Fe^{2+}$ toxin.

FIG. 2-b is a graph showing the results of combined treatment of compound obtained in Example 1 and $Zn^{2+}$ toxin.

FIG. 3-a is a graph showing the results of combined treatment of compound obtained in Example 2 and $Fe^{2+}$ toxin.

FIG. 3-b is a graph showing the results of combined treatment of compound obtained in Example 2 and $Zn^{2+}$ toxin.

FIG. 4-a is a graph showing the results of combined treatment of compound obtained in Example 3 and $Fe^{2+}$ toxin.

FIG. 4-b is a graph showing the results of combined treatment of compound obtained in Example 3 and $Zn^{2+}$ toxin.

FIG. 5-a is a graph showing the results of combined treatment of compound obtained in Example 4 and $Fe^{2+}$ toxin.

FIG. 5-b is a graph showing the results of combined treatment of compound obtained in Example 4 and $Zn^{2+}$ toxin.

FIG. 6-a is a graph showing the results of combined treatment of compound obtained in Example 5 and $Fe^{2+}$ toxin.

FIG. 6-b is a graph showing the results of combined treatment of compound obtained in Example 5 and $Zn^{2+}$ toxin.

FIG. 7-a is a graph showing the results of combined treatment of compound obtained in Example 6 and $Fe^{2+}$ toxin.

FIG. 7-b is a graph showing the results of combined treatment of compound obtained in Example 6 and $Zn^{2+}$ toxin.

FIG. 8-a is a graph showing the results of combined treatment of compound obtained in Example 7 and $Fe^{2+}$ toxin.

FIG. 8-b is a graph showing the results of combined treatment of compound obtained in Example 7 and $Zn^{2+}$ toxin.

FIG. 17-a is a graph showing the protection level of cell damage in case of the treatment of the compound of the invention after ischemia.

FIG. 17-b is a photomicrograph showing the protection level of cell damage in case of the treatment of the compound of the invention after ischemia.

DETAILED DESCRIPTION OF EMBODIMENTS

Figure 9:
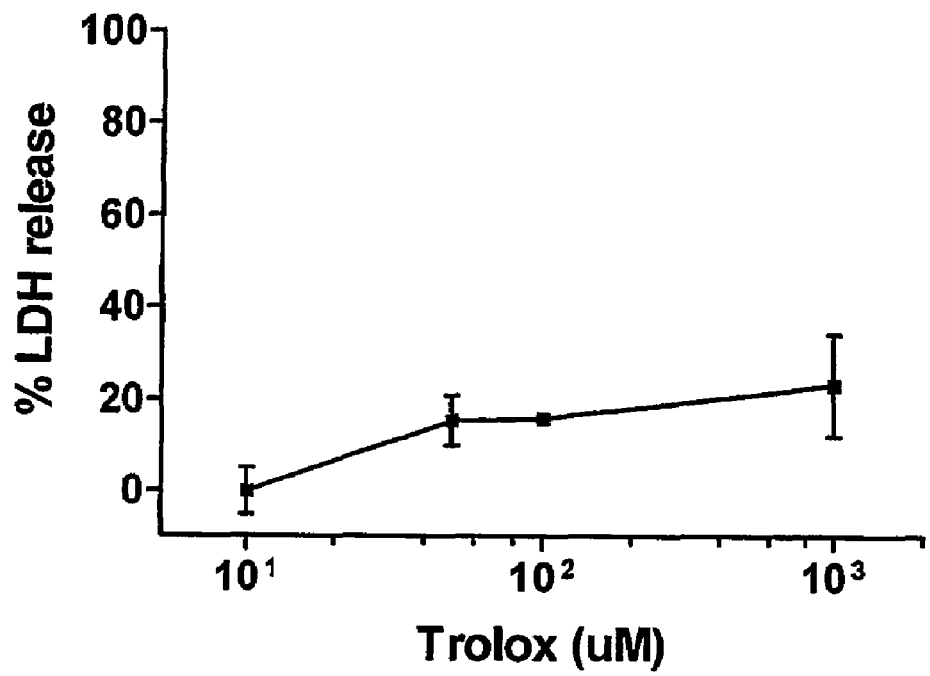
FIG. 9 is a graph showing the level of cell damage as the treatment concentration of Trolox increases.

In the first aspect, the present invention provides novel dialkyl hydroxybenzoic acid derivatives containing metal chelating groups with the following formula (I):

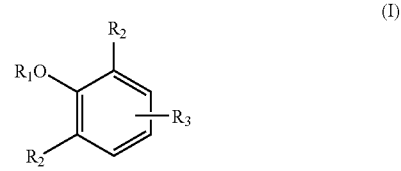

In the foregoing formula, $R_1$ denotes hydrogen, or a straight or branched acyl; $R_2$ denotes hydrogen or alkyl; and $R_3$ denotes metal chelating groups such as $CO_2H$, $CONH_2$, $CONR_4R_5$ (where, $R_4$ denotes hydrogen, alkyl or aryl; and, $R_5$ denotes heterocyclic unsaturated or saturated radical having 1 to 4 heteroatoms of elements nitrogen, oxygen and/or sulfur from the group comprising furanyl, oxazolyl, isooxazolyl, thiophenyl, thiazolyl, isothiazolyl, pyrrolyl, imidazolyl, pyrazolyl, oxadiazolyl, thiadiazolyl, pyridyl, pyrimidinyl, pyrazinyl, pyridazinyl, triazinyl, triazolyl, tetrazolyl, it being possible for the heterocyclic radical to be substituted once or twice, identically or differently, by halogen, $C_{1\sim2}$-alkyl, $C_{1\sim4}$-alkoxy, $C_{1\sim4}$-alkylthio, hydroxy, mercapto, trifluoromethyl, nitro, phenyl, nitrile, carboxy or $C_{1\sim4}$-alkoxycarbonyl).

In this context, preferred compounds include derivatives in which $R_1$ represents hydrogen, straight or branched $C_{1\sim18}$ alkyl carbonyl; $R_2$ represents hydrogen, straight or branched $C_{1\sim8}$-alkyl; and, $R_3$ represents $CO_2H$, $CONH_2$, or amides $CONR_4R_5$ (where, $R_4$ represents hydrogen, $C_{1\sim4}$-alkyl, aralkyl or cycloalkyl; and, $R_5$ denotes heterocyclic unsaturated or saturated radical having 1 to 4 heteroatoms of elements nitrogen, oxygen and/or sulfur from the group comprising furanyl, oxazolyl, isooxazolyl, thiophenyl, thiazolyl, isothiazolyl, pyrrolyl, imidazolyl, pyrazolyl, oxadiazolyl, thiadiazoyl, pyridyl, pyrimidinyl, pyrazinyl, pyridazinyl, triazinyl, triazolyl, tetrazolyl it being possible for the heterocyclic radical to be substituted once or twice, identically or differently, by halogen, $C_{1\sim2}$-alkyl, $C_{1\sim4}$-alkoxy, $C_{1\sim4}$-alkylthio, hydroxy, mercapto, trifluoromethyl, nitro, phenyl, nitrile, carboxy and/or $C_{1\sim4}$-alkoxycarbonyl).

More preferred compounds include derivatives in which $R_1$ represents hydrogen, acetyl, propionyl; $R_2$ represents hydrogen, methyl, ethyl, propyl, butyl, isopropyl, tert-butyl, cyclopentyl, cyclohexyl; and, $R_3$ represents $CO_2H$, $CONH_2$, or amides $CONR_4R_5$ (where, $R_4$ represents hydrogen, methyl, ethyl, propyl, benzyl, cyclopentyl or cyclohexyl; and, $R_5$ denotes heterocyclic unsaturated or saturated radical having 1 to 4 heteroatoms of elements nitrogen, oxygen and/or sulfur from the group comprising oxazolyl, thiazolyl, isothiazolyl, imidazolyl, pyrazolyl, thiadiazoyl, pyridyl, pyrimidinyl, pyrazinyl, pyridazinyl, triazinyl, triazolyl, tetrazolyl it being possible for the heterocyclic radical to be substituted once or twice, identically or differently, by fluorine, chlorine, bromine, methyl, methoxy, ethoxy, methylmercapto, hydroxy, mercapto, trifluoromethyl, nitro, phenyl, nitrile, carboxy, methoxycarbonyl and/or ethoxycarbonyl).

The compounds of the invention possess similar or better LPO inhibition activity to the reference compounds of Trolox and Ebselen. While showing lower toxicity, they also effectively inhibit the cerebral neuronal cell injury caused by ROS and/or zinc ion and shows neuroprotective effects against ischemic neuronal degeneration.

The compounds of the invention, particularly the compound synthesized in Example 4 below, have a very low toxicity $LD_{50} \geqq 6,950$ mg/kg in the case of oral administration in rats, and $\geqq 800$ mg/kg in the case of intraperitoneal administration in rats. Therefore, one of the advantages of the invention is that the novel compounds can be administered at vastly higher levels than certain other known antioxidants, such as Ebselen ($LD_{50}$ values of Ebselen obtained on mice were $\geqq 6,810$ mg/kg in the case of oral administration, and 740 mg/kg in the case of intraperitoneal administration. Similarly, the $LD_{50}$ values of Ebselen obtained on rats were $\geqq 6,810$ mg/kg in the case of oral administration and 580 mg/kg in the case of intraperitoneal administration). Accordingly, large doses of the subject compounds may be administered immediately post stroke or other trauma to significantly reduce oxidative damage in many cases.

In the second aspect, the present invention provides pharmaceutical compositions comprising pharmaceutically acceptable carrier and pharmaceutically effective amount of the compound of formula (I) above or pharmaceutically acceptable salts thereof. A neuroprotective agent comprising the compound of the formula (I) as active ingredient is preferably provided.

In the third aspect, the present invention provides a method for treating a living body afflicted with a condition requiring an antioxidant and/or metal chelating agent, in particular acute and progressive neurodegenerative disorders, comprising a step of administering to the living body said pharmaceutical composition.

As previously mentioned, the compounds of the present invention have been found to be effective in relieving various effects resulting from ROS and/or excess Zn ions. These compounds are useful as therapeutics for treating and/or preventing a wide variety of medical dysfunctions and diseases including, but not limited to, acute central nervous system (CNS) disorders and neurodegerative conditions.

The compounds of the invention, as pharmaceuticals, are typically administered in the form of a pharmaceutical composition comprising at least one active compound of the invention and a pharmaceutically acceptable carrier or vehicle suitable for use in pharmaceutical compositions.

In general, the compounds of the invention are administered in a pharmaceutically effective amount. The amount of the compound actually administered will typically be determined by a physician, in the light of relevant circumstances, including the condition to be treated, the chosen route of administration, the actual compound administered, the age, weight, and response of the individual patient, the severity of the patient's symptoms, and the like. The dosage used ranges from 10 mg to 500 mg in one or several administrations per day.

The pharmaceutical compositions of the invention can be administered by a variety of routes including oral, rectal, transdermal, subcutaneous, intravenous, intramuscular, and intranasal. Depending on the intended route of delivery, the compounds are preferably formulated as either injectable or oral compositions.

The compositions for oral administration can take the form of bulk liquid dilutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, dialkyl hydroxybenzoic acid derivatives containing metal chelating groups of the invention is usually a minor component (from about 0.1 to about 50% by weight or preferably from about 1 to about 40% by weight) with the remainder being various vehicles or carriers and processing acids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the present compound in such compositions is typically a minor component, often being from about 0.05 to 10% by weight with the remainder being the injectable carrier and the like.

The above described components for orally administrable or injectable compositions are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

The compounds of the invention can also be administered in sustained release forms or from sustained release drug delivery systems. A description of representative sustained release materials can be found in the incorporated materials in Remington's Pharmaceutical Sciences.

The following Examples are provided to illustrate the invention and are not to be construed in any way as limiting the scope of the invention.

EXAMPLE 1

Synthesis of 3,5-Di-tert-butyl-4-hydroxy-N-pyridin-2-yl-benzamide (2)

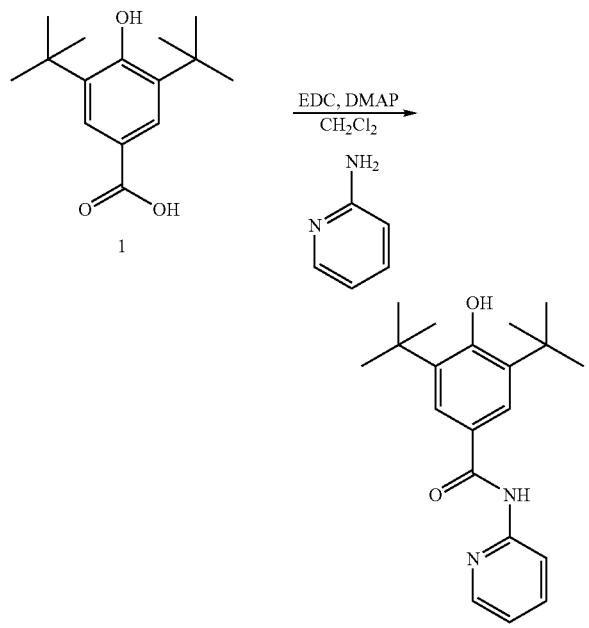

To a solution of 0.1 g (0.42 mmol) of compound 1 in CH$_2$Cl$_2$ (1 mL) were added 96 mg (0.50 mmol) of 1-(3-dimethylamino)propyl-3-ethylcarbodimide hydrochloride (EDC), 26 mg (0.21 mmol) of 4-dimethylaminopyridine (DMAP) and 60 mg (0.63 mmol) of 2-aminopyridine. After stirring for 12 hours at room temperature, H$_2$O and CH$_2$Cl$_2$ were added. The organic layer was separated, dried over anhydrous MgSO$_4$, filtered and concentrated under reduced pressure. The residue was purified by flash column chromatography (silica, Hex:EtOAc=8:1) to give 53 mg of compound 2 in 70% yield.

$^1$H NMR (CDCl$_3$): δ 8.68 (s, NH), 8.39 (d, 1H, J=8.4 Hz), 8.23 (d, 1H, J=2.4 Hz), 7.75 (s, 3H), 7.03 (t, 1H, J=6.9 Hz), 5.67 (s, OH), 1.47 (s, 18H);

$^{13}$C NMR (CDCl$_3$): δ 166.8, 157.9, 152.3, 148.1, 138.8, 136.6, 125.7, 124.9, 119.9, 114.5, 34.8, 30.5

EXAMPLE 2

Synthesis of 3,5-Di-tert-butyl-4-hydroxy-N-pyridin-2-yl methyl benzamide (3)

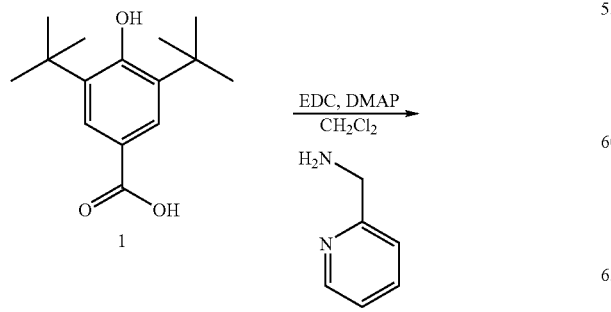

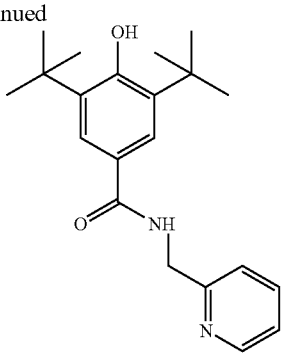

To a solution of 0.1 g (0.42 mmol) of compound 1 in CH$_2$Cl$_2$ (1 mL) were added 96 mg (0.50 mmol) of 1-(3-dimethylamino)propyl-3-ethylcarbodimide hydrochloride (EDC), 26 mg (0.21 mmol) of 4-dimethylaminopyridine and 0.07 mL (0.63 mmol) of 2-aminomethylpyridine. After stirring for 3 hours at room temperature, H$_2$O and CH$_2$Cl$_2$ were added. The organic layer was separated, dried over anhydrous MgSO$_4$, filtered and concentrated under reduced pressure. The residue was purified by flash column chromatography (silica, Hex:EtOAc=5:1) to give 110 mg of compound 3 in 80% yield.

$^1$H NMR (CDCl$_3$): δ 8.55 (d, 2H, J=4.8 Hz), 7.64 (s, 3H), 7.35 (d, 2H, J=8.0 Hz), 7.20 (t, 1H, J=5.4 Hz), 5.55 (s, OH), 4.75 (d, 2H, J=5.1 Hz), 1.46 (s, 18H);

$^{13}$C NMR (CDCl$_3$): δ 168.5, 157.3, 157.2, 149.5, 137.2, 136.2, 125.9, 124.66, 122.69, 45.3, 34.8, 30.5

EXAMPLE 3

Synthesis of 3,5-Di-tert-butyl-4-hydroxy-N-(8-hydroxyyquinolin-5-yl) benzamide (4)

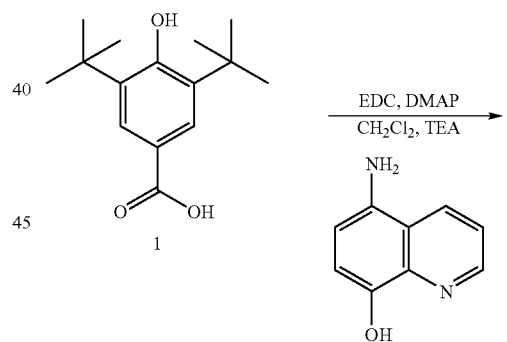

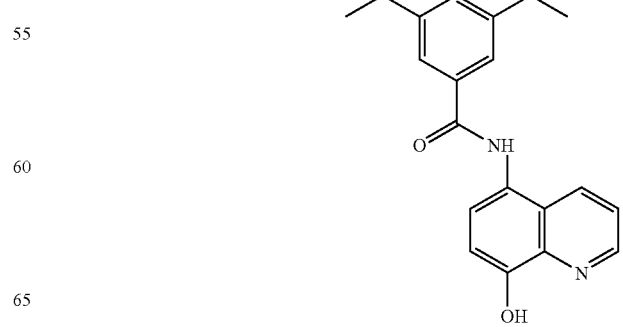

To a solution of 0.1 g (0.42 mmol) of compound 1 in CH$_2$Cl$_2$ (5 mL) were added 96 mg (0.50 mmol) of 1-(3-dimethylamino)propyl-3-ethyl carbodiimide hydrochloride (EDC), 26 mg (0.21 mmol) of 4-(dimethyl)-amino pyridine (DMAP), 2 mL of triethylamine and 147 mg (0.63 mmol) of 5-amino-8-hydroxyquinoline 2HCl salt. After stirring for 12 hours at room temperature, H$_2$O and CH$_2$Cl$_2$ were added. The organic layer was separated, dried over anhydrous MgSO$_4$, filtered and concentrated under reduced pressure. The residue was purified by flash column chromatography (silica, Hex:EtOAc=5:1) to give 64 mg of compound 4 in 40% yield.

$^1$H NMR (CDCl$_3$): δ 8.88 (s, 2H), 8.25 (s, 3H), 7.36 (t, 1H, J=6.8 Hz), 7.29 (d, 1H, J=9.3 Hz), 6.76 (d, 1H, J=8.1 Hz), 5.74 (s, OH), 4.18 (s, OH), 1.49 (s, 18H);

$^{13}$C NMR (CDCl$_3$): δ 179.0, 166.9, 159.0, 150.7, 140.8, 140.5, 136.2, 130.1, 128.5, 122.4, 120.9, 120.3, 120.0, 109.5, 34.8, 30.6

EXAMPLE 4

Synthesis of 3,5-Di-tert-butyl-4-hydroxy-N-thiazol-2-yl benzamide (5)

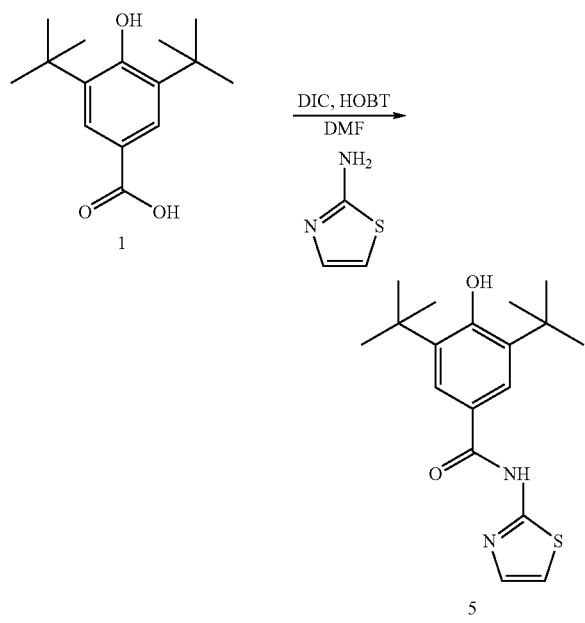

To a solution of 3.69 g (15.5 mmol) of compound 1 in DMF (5 mL) were added 2.9 mL (18.6 mmol) of diisopropylcarbodiimide (DIC), 2.85 g (18.6 mmol) of N-hydroxybenzotriazole (HOBT), and 2.33 g (23.3 mmol) of 2-aminothiazole. After stirring for 20 hours at room temperature, H$_2$O and EtOAc were added. The organic layer was separated, dried over anhydrous MgSO$_4$, filtered and concentrated under reduced pressure. The residue was purified by flash column chromatography (silica, Hex:EtOAc=5:1) to give 2 g of compound 5 in 70% yield.

$^1$H NMR (CDCl$_3$): δ 7.83 (s, 2H), 7.05 (d, 1H, J=3.6 Hz), 6.90 (d, 1H, J=3.6 Hz), 1.44 (s, 18H);

$^{13}$C NMR (CDCl$_3$): δ 166.5, 160.7, 158.2, 137.4, 125.6, 123.8, 113.3, 34.6, 30.2

EXAMPLE 5

Synthesis of 2-(3,5-Di-tert-butyl-4-hydroxy-benzoylamino)-thiazole-4-carboxylic acid ethyl ester (6)

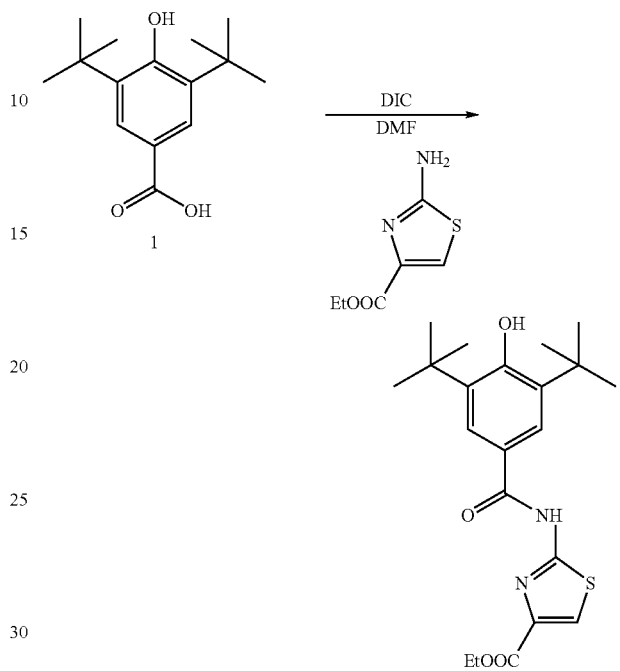

To a solution of 0.15 g (0.63 mmol) of compound 1 in DMF (1 mL) were added 0.12 mL (0.76 mmol) of diisopropylcarbodiimide (DIC), and 112 mg (0.95 mmol) of ethyl 2-aminothiazole-4-carboxylate. After stirring for 24 hours at room temperature, H$_2$O and CH$_2$Cl$_2$ were added. The organic layer was separated, dried over anhydrous MgSO$_4$, filtered and concentrated under reduced pressure. The residue was purified by flash column chromatography (silica, Hex:EtOAc=6:1) to give 74 mg of compound 6 in 30% yield.

$^1$H NMR (CDCl$_3$): δ 10.43 (s, NH), 7.86 (s, 1H), 7.77 (s, 2H), 5.76 (s, OH), 4.29 (q, 2H, J=11.5 Hz), 1.45 (s, 18H), 1.33 (t, 3H, J=7.1 Hz);

$^{13}$C NMR (CDCl$_3$): δ 165.7, 161.5, 159.3, 158.6, 141.8, 136.7, 125.2, 122.6, 122.4, 61.5, 34.6, 30.2, 14.4

EXAMPLE 6

Synthesis of 4-Hydroxy-3,5-dimethyl-N-pyridin-2-yl-benzamide (8)

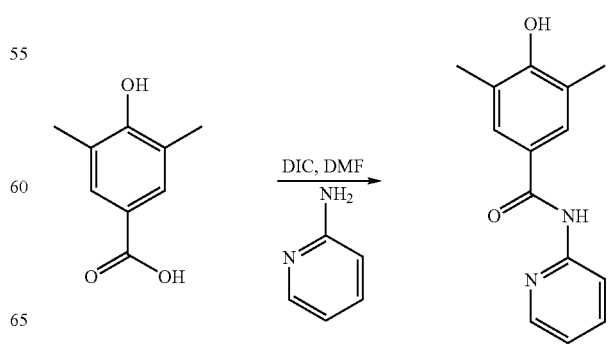

To a solution of 30 mg (0.18 mmol) of compound 7 in DMF (5 mL) were added 0.17 mL (0.21 mmol) of diisopropylcarbodiimide (DIC) and 17 mg (0.18 mmol) of 2-aminopyridine. After stirring for 10 hours at room temperature, saturated NaCl solution was added. The resulting mixture was extracted with EtOAc and the organic layer was washed with water and saturated NaCl solution several times. The organic layer was separated, dried over anhydrous $MgSO_4$, filtered and concentrated under reduced pressure. The residue was purified by flash column chromatography (silica, Hex: EtOAc=2:1) to give 4.4 mg of compound 8 in 10% yield.

$^1$H NMR ($CD_3CO_2D$): δ 8.43 (d, 1H, J=8.6 Hz), 8.30 (d, 1H, J=4.7 Hz), 8.06 (dd, 1H, J=7.4, 8.6 Hz), 7.74 (s, 2H), 7.30 (dd, 1H, J=6.3, 6.4 Hz), 2.29 (s, 6H);

$^{13}$C NMR ($CD_3CO_2D$): δ 168.66, 158.44, 152.16, 144.53, 142.90, 130.18, 125.07, 120.96, 117.44, 16.42

EXAMPLE 7

Synthesis of
4-Hydroxy-3,5-dimethyl-N-pyridine-2-yl methyl benzamide (9)

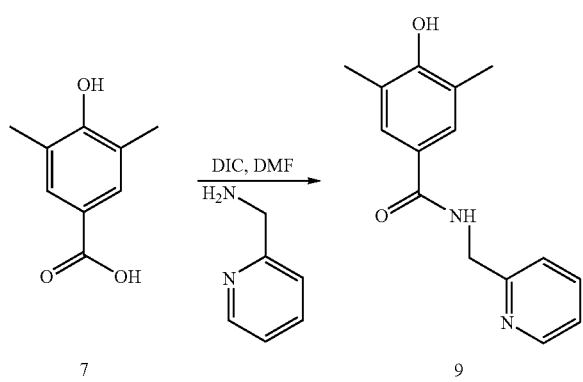

To a solution of 30 mg (0.18 mmol) of compound 7 in DMF (5 mL) were added 0.17 mL (0.21 mmol) of diisopropylcarbodiimide (DIC) and 19 mg (0.18 mmol) of 2-aminomethylpyridine. After stirring for 3.5 hours at room temperature, saturated NaCl solution was added. The resulting mixture was extracted with EtOAc and the organic layer was washed with water and saturated NaCl solution several times. The organic layer was separated, dried over anhydrous $MgSO_4$, filtered and concentrated under reduced pressure. The residue was purified by flash column chromatography (silica, Hex: EtOAc=2:1) to give 13.8 mg of compound 9 in 30% yield.

$^1$H NMR (DMSO-$d_6$): δ 8.81-8.72 (m, 2H), 8.49 (d, 1H, J=4.2 Hz), 7.73 (dd, 1H, J=0.3, 7.5 Hz), 7.53 (s, 2H), 7.27 (d, 1H, J=7.8 Hz), 7.24 (dd, 1H, J=5.8, 6.37 Hz);

$^{13}$C NMR (DMSO-$d_6$): δ 166.31, 159.20, 156.09, 148.74, 136.62, 127.76, 124.80, 123.63, 121.93, 120.78, 44.58, 16.64

Using the procedures described in Examples 1-7 above and the appropriate starting materials and reagents, the following dialkylhydroxybenzoic acid derivatives containing metal chelating groups could be prepared: 3,5-Dimethyl-4-hydroxy-N-furan-2-yl-benzamide; 3,5-Di-tert-butyl-4-hydroxy-N-furan-2-yl-benzamide; 3,5-Dimethyl-4-acetoxy-N-furan-2-yl-benzamide; 3,5-Di-tert-butyl-4-acetoxy-N-furan-2-yl-benzamide; 3,5-Dimethyl-4-hydroxy-N-oxazol-2-yl-benzamide; 3,5-Di-tert-butyl-4-hydroxy-N-oxazol-2-yl-benzamide; 3,5-Dimethyl-4-hydroxy-N-isoxazol-3-yl-benzamide; 3,5-Di-tert-butyl-4-hydroxy-isoxazol-3-yl-benzamide; 3,5-Dimethyl-4-hydroxy-N-thiophen-2-yl-benzamide; 3,5-Di-tert-butyl-4-hydroxy-N-thiophen-2-yl-benzamide; 3,5-Dimethyl-4-hydroxy-N-thiazol-2-yl-benzamide; 3,5-Di-tert-butyl-4-hydroxy-N-thiazol-2-yl-benzamide; 3,5-Dimethyl-4-hydroxy-N-isothiazol-3-yl-benzamide; 3,5-Di-tert-butyl-4-hydroxy-N-isothiazol-3-yl-benzamide; 3,5-Dimethyl-4-hydroxy-N-(1H-pyrrol-2-yl)-benzamide; 3,5-Di-tert-butyl-4-hydroxy-N-(1H-pyrrol-2-yl)-benzamide; 3,5-Dimethyl-4-hydroxy-N-(1-methyl-1H-pyrrol-2-yl)-benzamide; 3,5-Di-tert-butyl-4-hydroxy-N-(1-methyl-1H-pyrrol-2-yl)-benzamide; 3,5-Dimethyl-4-hydroxy-N-(1H-imidazol-2-yl)-benzamide; 3,5-Di-tert-butyl-4-hydroxy-(1H-imidazol-2-yl)-benzamide; 3,5-Dimethyl-4-hydroxy-N-(1-methyl-1H-imidazol-2-yl)-benzamide; 3,5-Di-tert-butyl-4-hydroxy-N-(1-methyl-1H-imidazol-2-yl)-benzamide; 3,5-Dimethyl-4-hydroxy-N-(2H-pyrazol-3-yl)-benzamide; 3,5-Di-tert-butyl-4-hydroxy-N-(2H-pyrazol-3-yl)-benzamide; 3,5-Dimethyl-4-hydroxy-N-(2-methyl-2H-pyrazol-3-yl)-benzamide; 3,5-Di-tert-butyl-4-hydroxy-N-(2-methyl-2H-pyrazol-3-yl)-benzamide; 3,5-Dimethyl-4-hydroxy-N-[1,3,4]oxadiazol-2-yl-benzamide; 3,5-Di-tert-butyl-4-hydroxy-N-[1,3,4]oxadiazol-2-yl-benzamide; 3,5-Dimethyl-4-hydroxy-N-[1,3,4]thiadiazol-2-yl-benzamide; 3,5-Di-tert-butyl-4-hydroxy-N-[1,3,4]thiadiazol-2-yl-benzamide; 3,5-Dimethyl-4-hydroxy-N-pyridin-2-yl-benzamide; 3,5-Di-tert-butyl-4-hydroxy-N-pyridin-2-yl-benzamide; 3,5-Dimethyl-4-hydroxy-N-pyrimidin-2-yl-benzamide; 3,5-Di-tert-butyl-4-hydroxy-N-pyrimidin-2-yl-benzamide; 3,5-Dimethyl-4-hydroxy-N-pyridazin-3-yl-benzamide; 3,5-Di-tert-butyl-4-hydroxy-N-pyridazin-3-yl-benzamide; 3,5-Dimethyl-4-hydroxy-N-pyrazin-2-yl-benzamide; 3,5-Di-tert-butyl-4-hydroxy-N-pyrazin-2-yl-benzamide; 3,5-Dimethyl-4-hydroxy-N-[1,3,5]triazin-2-yl-benzamide; 3,5-Di-tert-butyl-4-hydroxy-N-[1,3,5]triazin-2-yl-benzamide; 3,5-Dimethyl-4-hydroxy-N-(2H-[1,2,4]triazol-3-yl)-benzamide; 3,5-Di-tert-butyl-4-hydroxy-N-(2H-[1,2,4]triazol-3-yl)-benzamide; 3,5-Dimethyl-4-hydroxy-N-(2-methyl-2H-[1,2,4]triazol-3-yl)-benzamide; 3,5-Di-tert-butyl-4-hydroxy-N-(2-methyl-2H-[1,2,4]triazol-3-yl)-benzamide; 3,5-Dimethyl-4-hydroxy-N-(1H-tetrazol-5-yl)-benzamide; 3,5-Di-tert-butyl-4-hydroxy-N-(1H-tetrazol-5-yl)-benzamide; 3,5-Dimethyl-4-hydroxy-N-(1-methyl-1H-tetrazol-5-yl)-benzamide 3,5-Di-tert-butyl-4-hydroxy-N-(1-methyl-1H-tetrazol-5-yl)-benzamide;

EXAMPLE 8

Inhibition of Lipid Peroxidation

The compounds of the present invention were tested for antioxidizing effect in terms of the repression of the radical chain reaction of a multilayer liposome.

The liposome was prepared as followings: 30 mg of commercially available soybean phosphatidylcholine (PC, Sigma Chemical Co., U.S.A.) was dissolved in 1 mL of ethanol, and 200 μL of the ethanol/PC solution was added to 10 mL of 10 mM Tris buffer including 50 mM NaCl (pH 7.0) with stirring.

The ability of a compound to inhibit oxidation of the liposome was evaluated as followings: To 400 μL of the liposomes were added the test compound (in buffer or ethanol) and histidine-$FeCl_3$ (167:33 μM final). Oxidation was initiated by the addition of $FeCl_2$ (33 μM final prepared in nitrogen purged water). The mixtures was shaken at 37° C. for 15 minutes. Thereafter, tubes were treated with 1 mL of 0.67% thiobabituric acid (TBA):10% trichloroacetic acid (2:1, v/v) in 0.25 N HCl solution, containing 1.5% (v/v) t-butylhydroxytoluene (BHT) to terminate oxidation. The aliquots were heated to 100° C. for 20 minutes. After ice cooling, 1 mL of chloroform was added to 1 mL supernatant from tubes and tubes were centrifuged. The absorbances of the resulting supernatant were measured at 532 nm (see: Table below).

|  | Inhibitor Concentration ($IC_{50}$) |
|---|---|
| Example 1 | 11.88 μM |
| Example 2 | 12.65 μM |
| Example 3 | 7.79 μM |
| Example 4 | 9.69 μM |
| Example 5 | 11.10 μM |
| Example 6 | 121.50 μM |
| Example 7 | 299.5 μM |
| Ebselen | 68.86 μM |
| Trolox | 10.15 μM |

It can be seen from Table that the compounds of the present invention, especially compounds obtained in Example 1-5, have similar or superior LPO inhibition activity to the reference compounds, Trolox (vitamin E derivative, used as a reference material in numerous in vitro and in vivo antioxidant test) and Ebselen (the most promising antioxidant currently and is in clinical phase III).

EXAMPLE 9

Protection of Neuron Cells by the Compounds of the Invention

EXAMPLE 9-1

The Culture of Neuron Cells of Cerebral Cortex

Mixed cortical cell cultures, containing both neuronal and glial elements, were prepared from fetal ICR (Institute Cancer Research) mice at 14-15 days of gestation. Briefly, dissociated cortical cells were plated onto previously established glial monolayer culture at 2.5 hemispheres per 24-multiwell plate (Nunc, USA). The plating medium consisted of Eagle's minimal essential medium (Earle's salts, supplied glutamine-free) supplemented with glucose (final concentration, 20 mM), 2 mM glutamine, 5% fetal bovine serum, and 5% horse serum. Ten mM cytosine arabinoside was added to the medium 5-6 days after the plating to halt the growth of non-neuronal cells. Cultures were maintained at 37° C. in a humidified $CO_2$ incubator (5%) and used for experiments after between 10-14 days in vitro (DIV).

The glial feeder cultures were prepared from neocortices of postnatal (1-3 day-old) mice. Dissociated cortical cells were plated at 0.25 hemispheres per 24-multiwell plate, in plating medium supplemented with 5% fetal bovine serum, and 10% horse serum. With this method, most neurons do not survive, but astrocytes do, resulting in astrocyte-rich cultures. Glial cultures were grown to confluency for 10-30 days, when they were used to generate mixed cortical cultures.

EXAMPLE 9-2

Protection of Cortical Neuronal Cell Death Induced by $Fe^{2+}$ Ion and $Zn^{2+}$ Ion When ferrous iron is placed in normoxic solution, it autooxidizes to produce ROS in the form of hydroxyl radicals, superoxide anion free radicals, and hydrogen peroxide.

Cortical cell cultures prepared in Example 9-1 were exposed for 24 hours to 30 μM $FeCl_2$ (Fe) or 35 μM $ZnCl_2$ (Zn, neuro-excitotoxic factor), to induce neuronal cell death. Twenty four hour exposure to toxin with or without test compounds was done in serum free Eagle's minimal essential medium (MEM) supplemented with 20 mM glucose and 38 mM sodium bicarbonate in 5% $CO_2$ incubator at 37° C. All of compounds were dissolved in DMSO at high concentrations, and then diluted to final concentrations in the exposure medium at the time of addition.

Methods of measuring cell death were now discussed. Overall cell injury was first estimated in all experiments by examination of cultures under phase-contrast microscope. The morphological assessments were usually performed one day after exposure to toxins, at which point the process of cell death was largely completed.

In addition, overall neuronal cell injury was quantitatively estimated by measuring the activity of lactate dehydrogenase (LDH), released by damaged or destroyed cells, into the extracellular fluid. A small amount of LDH was always present in the media of cultures that underwent the same exposure procedures but without the addition of toxins (sham wash controls). This background amount, determined on sister sham wash controls within each experiment, was subtracted from values obtained in toxin-treated cultures. The absolute value of the LDH efflux produced by toxin exposure was quite consistent within sister cultures of single plating, but varied somewhat in cultures of different platings. This variability is largely a function of resultant neuronal density (which varied despite constant original plating densities, presumably reflecting small variations in cell preparation or serum characteristics). Therefore, each LDH value was scaled to the maximal neuronal LDH release (=100) after 24 hours exposure to 30 μM $FeCl_2$ (Fe) or 35 μM $ZnCl_2$ (Zn), in sister cultures, where near complete neuronal death with no glial damage occurs. Numbers greater than 100 usually indicate additional astroglial cell injury.

FIG. 1-a is a graph showing the results of combined treatment of Trolox and $Fe^{2+}$ toxin.

FIG. 1-b is a graph showing the results of combined treatment of Trolox and $Zn^{2+}$ toxin.

FIG. 2-a is a graph showing the results of combined treatment of compound obtained in Example 1 and $Fe^{2+}$ toxin.

FIG. 2-b is a graph showing the results of combined treatment of compound obtained in Example 1 and $Zn^{2+}$ toxin.

FIG. 3-a is a graph showing the results of combined treatment of compound obtained in Example 2 and $Fe^{2+}$ toxin.

FIG. 3-b is a graph showing the results of combined treatment of compound obtained in Example 2 and $Zn^{2+}$ toxin.

FIG. 4-a is a graph showing the results of combined treatment of compound obtained in Example 3 and $Fe^{2+}$ toxin.

FIG. 4-b is a graph showing the results of combined treatment of compound obtained in Example 3 and $Zn^{2+}$ toxin.

FIG. 5-a is a graph showing the results of combined treatment of compound obtained in Example 4 and $Fe^{2+}$ toxin.

FIG. 5-b is a graph showing the results of combined treatment of compound obtained in Example 4 and $Zn^{2+}$ toxin.

FIG. 6-a is a graph showing the results of combined treatment of compound obtained in Example 5 and $Fe^{2+}$ toxin.

FIG. 6-b is a graph showing the results of combined treatment of compound obtained in Example 5 and $Zn^{2+}$ toxin.

FIG. 7-a is a graph showing the results of combined treatment of compound obtained in Example 6 and $Fe^{2+}$ toxin.

FIG. 7-b is a graph showing the results of combined treatment of compound obtained in Example 6 and $Zn^{2+}$ toxin.

FIG. 8-a is a graph showing the results of combined treatment of compound obtained in Example 7 and $Fe^{2+}$ toxin.

FIG. 8-b is a graph showing the results of combined treatment of compound obtained in Example 7 and $Zn^{2+}$ toxin.

As seen from FIGS. 1-a to 8-b, the compounds of the present invention effectively protected the neuron cell injury induced by $Fe^{2+}$ or $Zn^{2+}$ toxin. Therefore, the compounds of the invention can be used as neuroprotective agents in order to protect cerebral neuron cells from ROS and/or excess Zn ions (neuro-excitotoxic factor).

EXAMPLE 10

Toxicity of the Compounds on the Neuron Cells

The viability of cortical cell prepared in Example 9-1 was quantified by lactate dehydrogenase (LDH) assay after exposure for 24 hours to the different concentrations of the test compound. Twenty four hours exposure to the compound was done in serum free Eagle's minimal essential medium (MEM) supplemented with 20 mM glucose and 38 mM sodium bicarbonate in 5% $CO_2$ incubator at 37° C. All of compounds were dissolved in DMSO at high concentrations, and then diluted to final concentrations in the exposure medium at the time of addition.

Measurement of cell death was the same as the method in the Example 9-2.

FIG. 9 is a graph showing the level of cell damage as the treatment concentration of Trolox increases.

Figure 10:
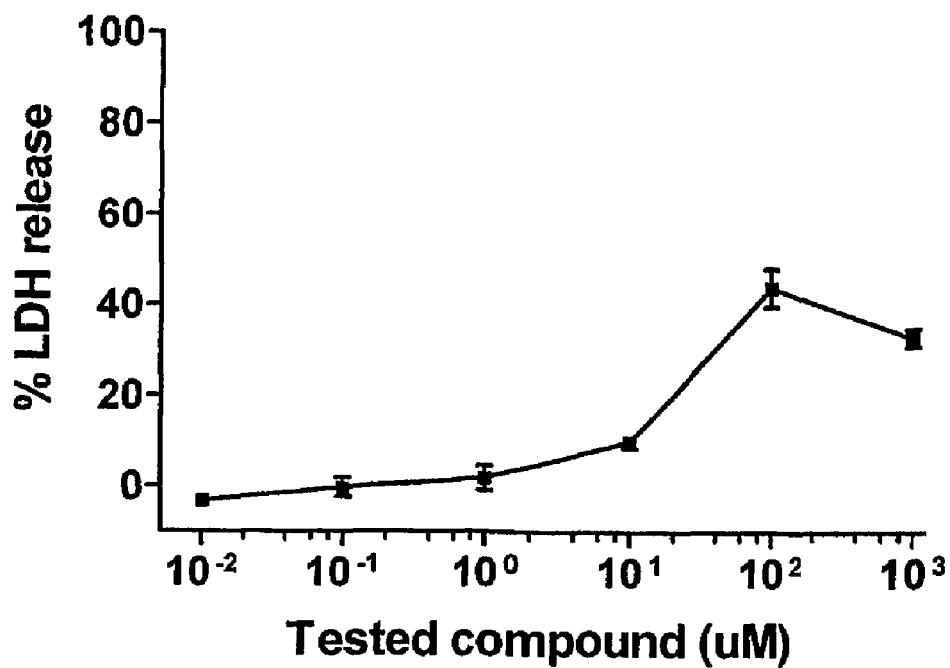
FIG. 10 is a graph showing the level of cell damage as the treatment concentration of compound obtained in Example 1 increases.

FIG. 10 is a graph showing the level of cell damage as the treatment concentration of compound obtained in Example 1 increases.

Figure 11:
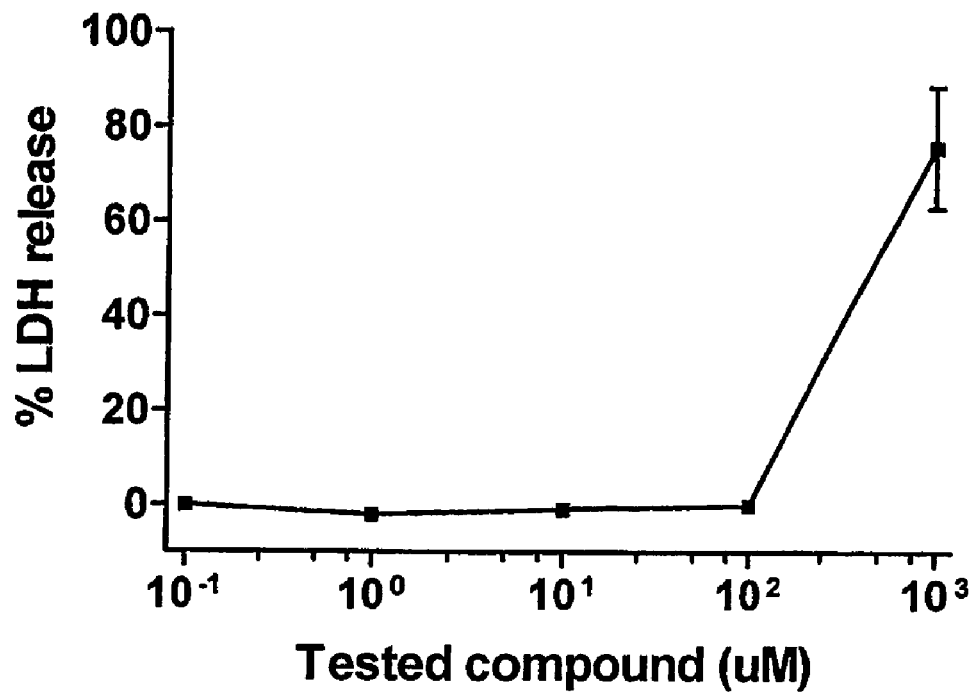
FIG. 11 is a graph showing the level of cell damage as the treatment concentration of compound obtained in Example 2 increases.

FIG. 11 is a graph showing the level of cell damage as the treatment concentration of compound obtained in Example 2 increases.

Figure 12:
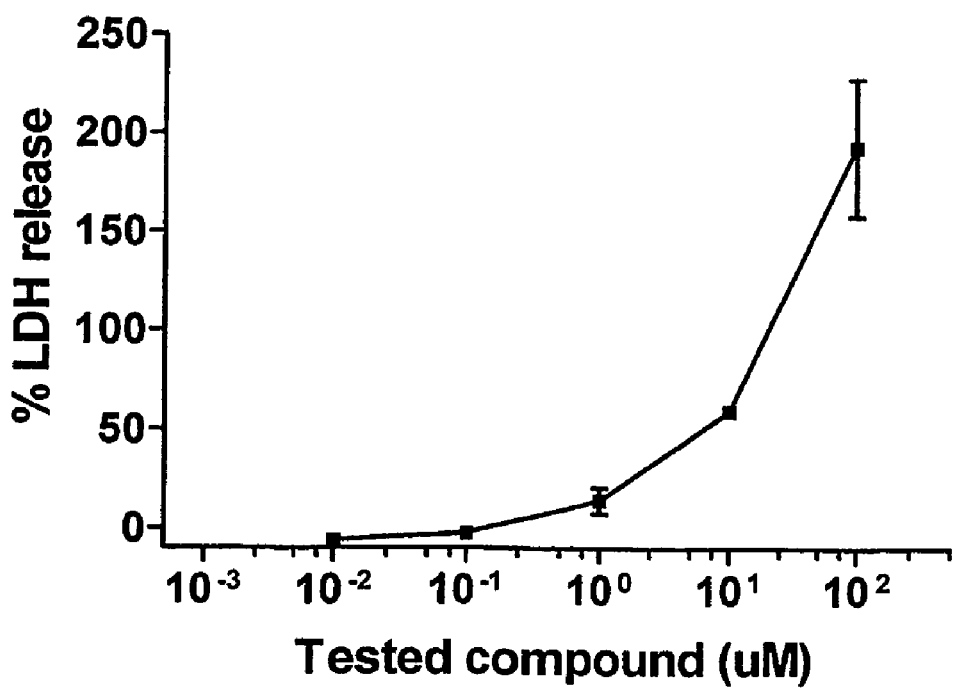
FIG. 12 is a graph showing the level of cell damage as the treatment concentration of compound obtained in Example 3 increases.

FIG. 12 is a graph showing the level of cell damage as the treatment concentration of compound obtained in Example 3 increases.

Figure 13:
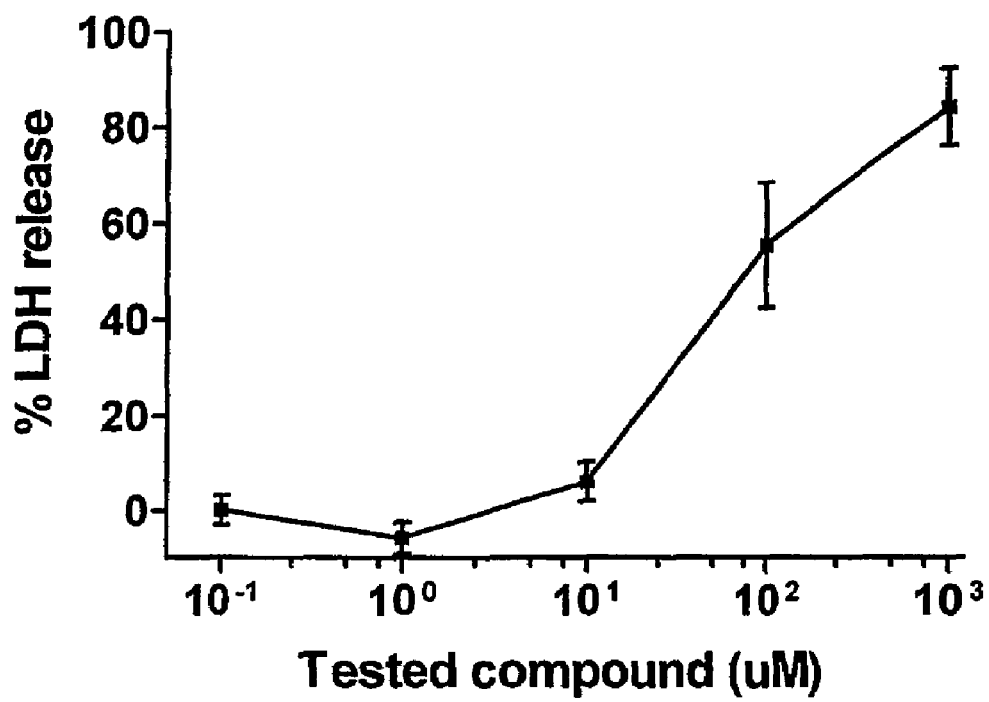
FIG. 13 is a graph showing the level of cell damage as the treatment concentration of compound obtained in Example 4 increases.

FIG. 13 is a graph showing the level of cell damage as the treatment concentration of compound obtained in Example 4 increases.

Figure 14:
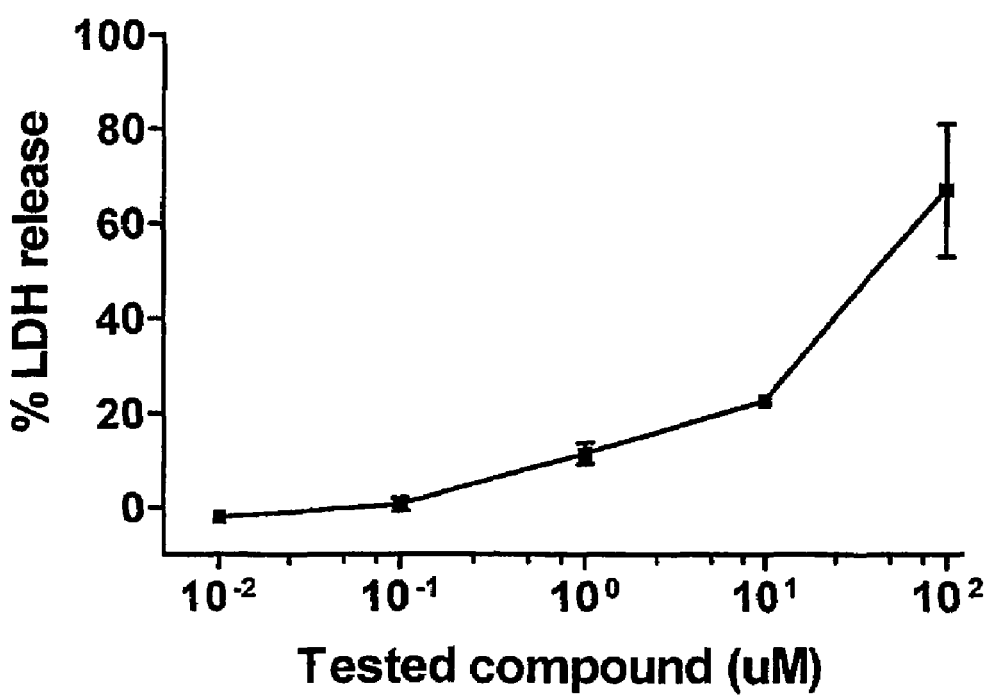
FIG. 14 is a graph showing the level of cell damage as the treatment concentration of compound obtained in Example 5 increases.

FIG. 14 is a graph showing the level of cell damage as the treatment concentration of compound obtained in Example 5 increases.

Figure 15:
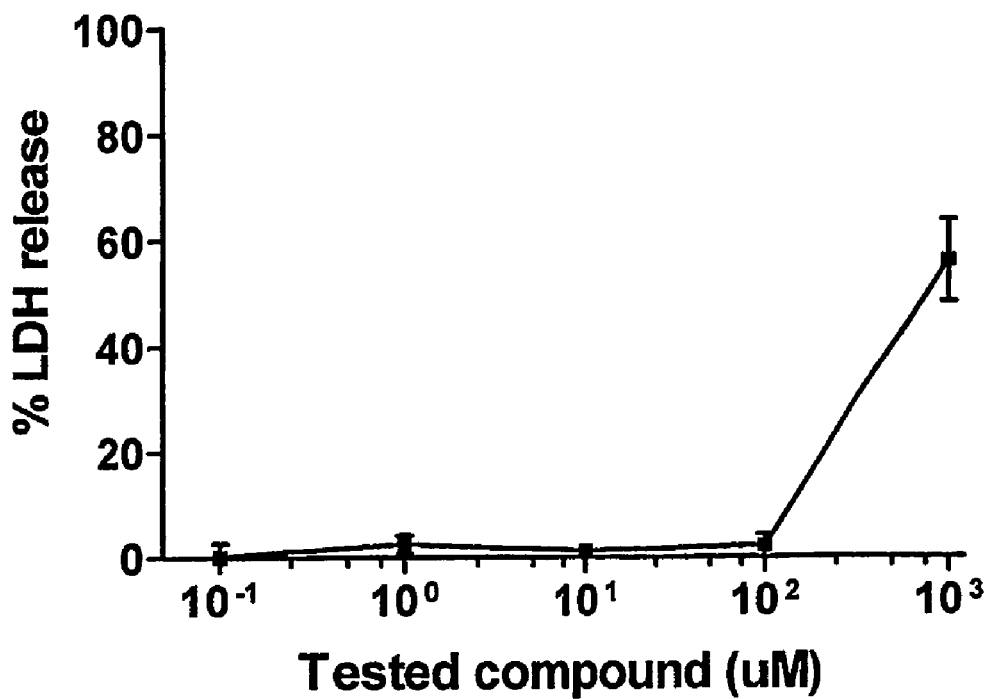
FIG. 15 is a graph showing the level of cell damage as the treatment concentration of compound obtained in Example 6 increases.

FIG. 15 is a graph showing the level of cell damage as the treatment concentration of compound obtained in Example 6 increases.

Figure 16:
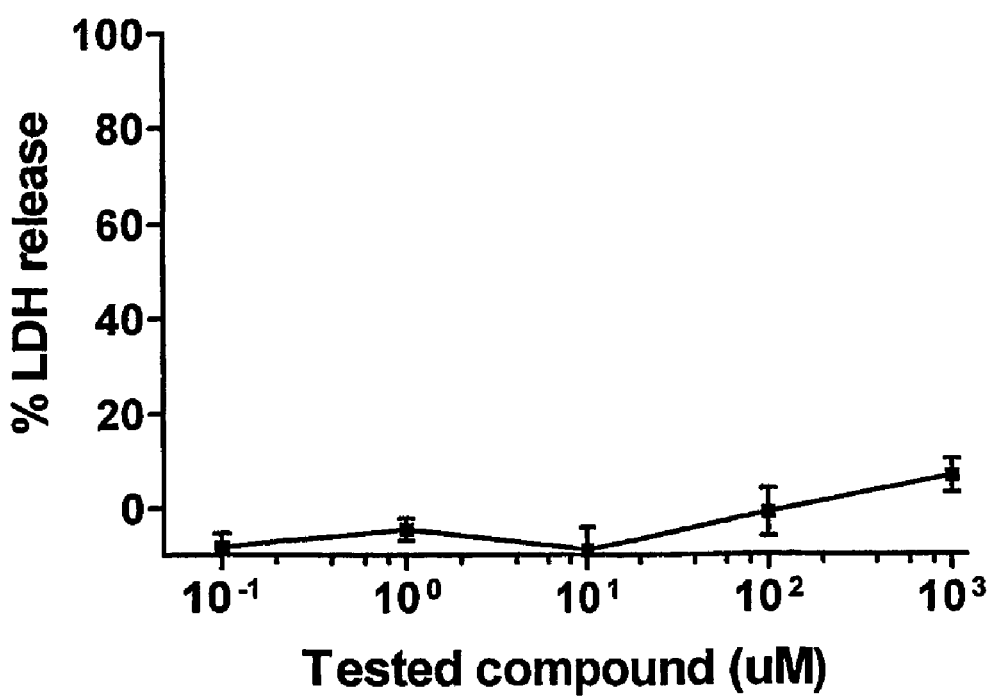
FIG. 16 is a graph showing the level of cell damage as the treatment concentration of compound obtained in Example 7 increases.

FIG. 16 is a graph showing the level of cell damage as the treatment concentration of compound obtained in Example 7 increases.

As seen from FIGS. 9 to 16, the compounds of the present invention exhibit low cytotoxicity. Accordingly, the new compounds of the present invention can be administered at large doses.

EXAMPLE 11

Protection of Cell Damage by Ischemia (In Vivo)

Male Mongolian gerbils (Meriones unguiculatus) weighing 80-88 g were used in the present study. Each animal was medicated P.O. with vehicle, Ebselen or various test compounds (60 mg/kg in 10% DMSO), after 30 minutes ischemic injury, respectively. 20 animals were allotted into every group. The animals were placed under general anesthesia with a mixture of 2.5% isoflurane in 33% oxygen and 67% nitrous oxide. A midline ventral incision was made in the neck. Both common carotid arteries were isolated, freed of nerve fibers, and occluded using nontraumatic aneurysm clips. Complete interruption of blood flow was confirmed by observing the central artery in eyeballs using ophthalmoscope. After five minutes of occlusion, the aneurysm clips were removed from both common carotid arteries. Restoration of blood flow (reperfusion) was observed directly under the microscope. Sham-operated controls were subjected to the same surgical procedures except that common carotid arteries were not occluded. Body temperature was monitored and maintained at 37° C.±0.5° C. during surgery and during the immediate postoperative period until the animals recovered fully from anesthesia. At the designated reperfusion time (4 days), operated animals and sham animals were killed.

Animals were perfused transcardially with phosphate-buffered saline (PBS, pH 7.4) followed by 4% paraformaldehyde in 0.1 M phosphate buffer (pH 7.4) at 4 days (n=7) after surgery. The brains were removed, and postfixed in the same fixative for 4 hours. The brain tissues were cryoprotected by infiltration with 30% sucrose overnight. Cornoy fixed specimens were cut into 30 μm sections on a cryostat. The sections were sequentially stained by Cresyl violet dye.

Images of staining in the hippocampus of each animal were captured with an Applescanner. The brightness and contrast of each image file were uniformly enhanced by Adobe Photoshop version 2.4.1, followed by analysis using NIH Image 1.59 software. All data obtained from the quantitative data were analyzed using one-way ANOVA to determine statistical significance. Bonferroni's test was used for post-hoc comparisons. P values below 0.05 or 0.01 were considered statistically significant.

FIG. 17-a is a graph showing the protection level of cell damage in case of the treatment of the compound of the invention after ischemia.

FIG. 17-b is a photomicrograph showing the protection level of cell damage in case of the treatment of the compound of the invention after ischemia.

As the results, the test compound prepared in Example 4 has more neuroprotective effects against ischemic neuronal degeneration than those of Ebselen. The compound synthesized in Example 4 showed that the protective effect was 91% in pre-treated groups. In the Ebselen-pretreated groups, the effect was 69%.

In conclusion, we suggest that the compound prepared in Example 4 may be an effective candidate as a preventive drug against ischemia, together with as a treatment drug against ischemia.

As described in detail and illustrated above, the invention provides novel dialkylhydroxybenzoic acid derivatives containing metal chelating groups, and the use of said novel compounds as therapeutics for treating and/or preventing various medical diseases arising from ROS and/or excess Zn ions. The compounds of the invention possess similar or superior lipid peroxidation (LPO) inhibition activity to the reference compounds of Trolox and Ebselen. While showing lower toxicity, they also effectively inhibit the cerebral neuronal cell death caused by ROS and/or zinc ion and show neuroprotective effects against ischemic neuronal degeneration.

From the foregoing description, various modifications and changes in the compositions and methods of the invention will occur to those skilled in the art. All such modifications coming within the scope of the appended claims are intended to be included therein.

What is claimed is:

1. A compound of the following formula (I) or a pharmaceutically acceptable salt thereof:

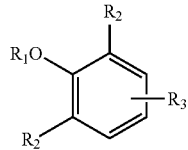

(I)

wherein $R_1$ denotes hydrogen, or a straight or branched acyl;
wherein $R_2$ denotes alkyl, and
wherein $R_3$ denotes $CO_2H$, $CONH_2$, or $CONR_4R_5$, wherein when $R_3$ is $CO_2$ or $CONH_2$, $R_1$ is straight or branched acyl, wherein $R_4$ denotes hydrogen, alkyl, aralkyl or aryl, and wherein $R_5$ denotes substituted or unsubstituted heterocyclic radical having 1 to 4 heteroatoms selected from the group consisting of nitrogen, oxygen and sulfur, the heterocyclic radical being selected from the group consisting of furanyl, oxazolyl, isooxazolyl, thiophenyl, thiazolyl, isothiazolyl, pyrrolyl, imidazolyl, pyrazolyl, oxadiazolyl, thiadiazoyl, pyridyl, pyrimidinyl, pyrazinyl, pyridazinyl, triazinyl, triazolyl, hydroxyguinolinyl, and tetrazolyl, it being possible for the heterocyclic radical to be substituted once or twice, identically or differently, by halogen, $C_{1-2}$-alkyl, $C_{1-4}$-alkoxy, $C_{1-4}$-alkylthio, hydroxy, mercapto, trifluoromethyl, nitro, phenyl, nitrile, carboxy, carboxylic ethyl ester or $C_{1-4}$-alkoxycarbonyl.

2. The compound of claim 1, wherein the acyl of $R_1$ comprises $C_{1-18}$ alkylcarbonyl.

3. The compound of claim 1, wherein the acyl of $R_1$ comprises acetyl or propionyl.

4. The compound of claim 1, wherein the alkyl of $R_2$ comprises straight or branched $C_{1-8}$ alkyl or cycloalkyl.

5. The compound of claim 1, wherein $R_2$ is selected from the group consisting of methyl, ethyl, propyl, butyl, isopropyl, tert-butyl, cyclopentyl and cyclohexyl.

6. The compound of claim 1, wherein the alkyl of $R_4$ comprises $C_{1-4}$ alkyl, or cycloalkyl.

7. A chemical compound or a pharmaceutically acceptable salt thereof, wherein the compound is selected from the group consisting of:
3,5-Dimethyl-4-hydroxy-N-(furan-2-yl)-benzamide;
3,5-Di-(tert-butyl)-4-hydroxy-(N-furan-2-yl)-benzamide;
3,5-Dimethyl-4-acetoxy-N-(furan-2-yl)-benzamide;
3,5-Di-(tert-butyl)-4-acetoxy-(N-furan-2-yl)-benzamide;
3,5-Dimethyl-4-hydroxy-N-(oxazol-2-yl)-benzamide;
3,5-Di-(tert-butyl)-4-hydroxy-N-(oxazol-2-yl)-benzamide;
3,5-Dimethyl-4-hydroxy-N-(isoxazol-3-yl)-benzamide;
3,5-Di-(tert-butyl)-4-hydroxy-(isoxazol-3-yl)-benzamide;
3,5-Dimethyl-4-hydroxy-N-(thiophen-2-yl)-benzamide;
3,5-Di-(tert-butyl)-4-hydroxy-N-(thiophen-2-yl)-benzamide;
3,5-methyl-4-hydroxy-N-(thiazol-2-yl)-benzamide;
3,5-Di-(tert-butyl)-4-hydroxy-N-(thiazol-2-yl)-benzamide;
3,5-Dimethyl-4-hydroxy-N-(isothiazol-3-yl)-benzamide;
3,5-Di-(tert-butyl)-4-hydroxy-N-(isothiazol-3-yl)-benzamide;
3,5-Dimethyl-4-hydroxy-N-(1H-pyrrol-2-yl)-benzamide;
3,5-Di-(tert-butyl)-4-hydroxy-N-(1H-pyrrol-2-yl)-benzamide;
3,5-Dimethyl-4-hydroxy-N-(1-methyl-1H-pyrrol-2-yl)-benzamide;
3,5-Di-(tert-butyl)-4-hydroxy-N-(1-methyl-1H-pyrrol-2-yl)-benzamide;
3,5-Dimethyl-4-hydroxy-N-(1H-imidazol-2-yl)-benzamide
3,5-Di-tert-butyl-4-hydroxy-(1H-imidazol-2-yl)-benzamide
3,5-Dimethyl-4-hydroxy-N-(1-methyl-1H-imidazol-2-yl)-benzamide
3,5-Di-tert-butyl-4-hydroxy-N-(1-methyl-1H-imidazol-2-yl)-benzamide
3,5-Dimethyl-4-hydroxy-N-(2H-pyrazol-3-yl)-benzamide;
3,5-Di-(tert-butyl)-4-hydroxy-N-(2H-pyrazol-3-yl)-benzamide;
3,5-Dimethyl-4-hydroxy-N-(2-methyl-2H-pyrazol-3-yl)-benzamide;
3,5-Di-(tert-butyl)-4-hydroxy-N-(2-methyl-2H-pyrazol-3-yl)-benzamide;
3,5-Dimethyl-4-hydroxy-N-([1,3,4]oxadiazol-2-yl)-benzamide;
3,5-Di-(tert-butyl)-4-hydroxy-N-([1,3,4]oxadiazol-2-yl)-benzamide;
3,5-Dimethyl-4-hydroxy-N-([1,3,4]thiadiazol-2-yl)-benzamide;
3,5-Di-(tert-butyl)-4-hydroxy-N-([1,3,4]thiadiazol-2-yl)-benzamide;
3,5-Dimethyl-4-hydroxy-N-(pyridin-2-yl)-benzamide;
3,5-Di-(tert-butyl)-4-hydroxy-N-(pyridin-2-yl)-benzamide;
3,5-Dimethyl-4-hydroxy-N-(pyrimidin-2-yl)-benzamide;
3,5-Di-(tert-butyl)-4-hydroxy-N-(pyrimidin-2-yl)-benzamide;
3,5-Dimethyl-4-hydroxy-N-(pyridazin-3-yl)-benzamide;
3,5-Di-(tert-butyl)-4-hydroxy-N-(pyridazin-3-yl)-benzamide;
3,5-Dimethyl-4-hydroxy-N-(pyrazin-2-yl)-benzamide;
3,5-Di-(tert-butyl)-4-hydroxy-N-(pyrazin-2-yl)-benzamide;
3,5-Dimethyl-4-hydroxy-N-([1,3,5]triazin-2-yl)-benzamide;
3,5-Di-(tert-butyl)-4-hydroxy-N-([1,3,5]triazin-2-yl)-benzamide;
3,5-Dimethyl-4-hydroxy-N-(2H-[1,2,4]triazol-3-yl)-benzamide;
3,5-Di-(tert-butyl)-4-hydroxy-N-(2H-[1,2,4]triazol-3-yl)-benzamide;
3,5-Dimethyl-4-hydroxy-N-(2-methyl-2H-[1,2,4]triazol-3-yl)-benzamide;
3,5-Di-(tert-butyl)-4-hydroxy-N-(2-methyl-2H-[1,2,4]triazol-3-yl)-benzamide;
3,5-Dimethyl-4-hydroxy-N-(1H-tetrazol-5-yl)-benzamide;
3,5-Di-(tert-butyl)-4-hydroxy-N-(1H-tetrazol-5-yl)-benzamide;
3,5-Dimethyl-4-hydroxy-N-(1-methyl-1H-tetrazol-5-yl)-benzamide;
3,5-Di-(tert-butyl)-4-hydroxy-N-(1-methyl-1H-tetrazol-5-yl)-benzamide;
3,5-Di-(tert-butyl)-4-hydroxy-N-(8-hydroxyquinolin-5-yl)-benzamide;
2-(3,5-Di-(tert-butyl)-4-hydroxy-benzoylamino)-thiazole-4-carboxylic acid ethyl ester;

3,5-Di-(tert-butyl)-4-hydroxy-N-(pyridin-2-yl)- methyl benzamide, and 3,5-Dimethyl-4-hydroxy-N-(pyridine-2-yl) methyl benzamide.

8. The compound of claim 1, wherein $R_3$ is a metal chelating group.

9. A pharmaceutical composition comprising:
one or more pharmaceutically acceptable carriers or excipients, and
an effective amount of the compound of claim 1 formula (I) or a pharmaceutically acceptable salt thereof.

10. The pharmaceutical composition of claim 9, wherein the carrier is an oral carrier.

11. The pharmaceutical composition of claim 9, wherein the carrier is an injectable carrier.

12. The pharmaceutical composition of claim 9, wherein the compound of formula (1) is selected from the group consisting of:

3,5-Dimethyl-4-hydroxy-N-(furan-2-yl)-benzamide;
3,5-Di-((tert-butyl)-4-hydroxy-(N-furan-2-yl)-benzamide;
3,5-Dimethyl-4-acetoxy-N-(furan-2-yl)-benzamide;
3,5-Di-(tert-butyl)-4-acetoxy-(N-furan-2-yl)-benzamide;
3,5-Dimethyl-4-hydroxy-N-(oxazol-2-yl)-benzamide;
3,5-Di-(tert-butyl)-4-hydroxy-N-(oxazol-2-yl)-benzamide;
3,5-Dimethyl-4-hydroxy-N-(isoxazol-3-yl)-benzamide;
3,5-Di-(tert-butyl)-4-hydroxy-(isoxazol-3-yl)-benzamide;
3,5-Dimethyl-4-hydroxy-N-(thiophen-2-yl)-benzamide;
3,5-Di-(tert-butyl)-4-hydroxy-N-(thiophen-2-yl)-benzamide;
3,5-methyl-4-hydroxy-N-(thiazol-2-yl)-benzamide;
3,5-Di-(tert-butyl)-4-hydroxy-N-(thiazol-2-yl)-benzamide;
3,5-Dimethyl-4-hydroxy-N-(isothiazol-3-yl)-benzamide;
3,5-Di-(tert-butyl)-4-hydroxy-N-(isothiazol-3-yl)-benzamide;
3,5-Dimethyl-4-hydroxy-N-(1H-pyrrol-2-yl)-benzamide;
3,5-Di-(tert-butyl)-4-hydroxy-N-(1H-pyrrol-2-yl)-benzamide;
3,5-Dimethyl-4-hydroxy-N-(1-methyl-1H-pyrrol-2-yl)-benzamide;
3,5-Di-(tert-butyl)-4-hydroxy-N-(1-methyl-1H-pyrrol-2-yl)-benzamide;
3,5-Dimethyl-4-hydroxy-N-(1H-imidazol-2-yl)-benzamide
3,5-Di-tert-butyl-4-hydroxy-(1H-imidazoi-2-yl)-benzamide
3,5-Dimethyl-4-hydroxy-N-(1-methyl-1H-imidazoi-2-yl)-benzamide
3,5-Di-tert-butyl-4-hydroxy-N-(1-methyl-1H-imidazol-2-yl)-benzamide
3,5-Dimethyl-4-hydroxy-N-(2H-pyrazol-3-yl)-benzamide;
3,5-Di-(tert-butyl)-4-hydroxy-N-(2H-pyrazol-3-yl)-benzamide;
3,5-Dimethyl-4-hydroxy-N-(2-methyl-2H-pyrazol-3-yl)-benzamide;
3,5-Di-(tert-butyl)-4-hydroxy-N-(2-methyl-2H-pyrazol-3-yl)-benzamide;
3,5-Dimethyl-4-hydroxy-N-([1,3,4]oxadiazol-2-yl)-benzamide;
3,5-Di-(tert-butyl)-4-hydroxy-N-([1,3,4]oxadiazol-2-yl)-benzamide;
3,5-Dimethyl-4-hydroxy-N-([1,3,4]thiadiazol-2-yl)-benzamide;
3,5-Di-(tert-butyl)-4-hydroxy-N-([1,3,4]thiadiazol-2-yl)-benzamide;
3,5-Dimethyl-4-hydroxy-N-(pyridin-2-yl)-benzamide;
3,5-Di-(tert-butyl)-4-hydroxy-N-(pyridin-2-yl)-benzamide;
3,5-Dimethyl-4-hydroxy-N-(pyrimidin-2-yl)-benzamide;
3,5-Di-(tert-butyl)-4-hydroxy-N-(pyrimidin-2-yl)-benzamide;
3,5-Dimethyl-4-hydroxy-N-(pyridazin-3-yl)-benzamide;
3,5-Di-(tert-butyl)-4-hydroxy-N-(pyridazin-3-yl)-benzamide;
3,5-Dimethyl-4-hydroxy-N-(pyrazin-2-yl)-benzamide;
3,5-Di-(tert-butyl)-4-hydroxy-N-(pyrazin-2-yl)-benzamide;
3,5-Dimethyl-4-hydroxy-N-([1,3,5]triazin-2-yl)-benzamide;
3,5-Di-(tert-butyl)-4-hydroxy-N-([1,3,5]triazin-2-yl)-benzamide;
3,5-Dimethyl-4-hydroxy-N-(2H-[1,2,4]triazol-3-yl)-benzamide;
3,5-Di-(tert-butyl)-4-hydroxy-N-(2H-[1,2,4]triazol-3-yl)-benzamide;
3,5-Dimethyl-4-hydroxy-N-(2-methyl-2H-[1,2,4]triazol-3-yl)-benzamide;
3,5-Di-(tert-butyl)-4-hydroxy-N-(2-methyl-2H-[1,2,4]triazol-3-yl)-benzamide;
3,5-Dimethyl-4-hydroxy-N-(1H-tetrazol-5-yl)-benzamide;
3,5-Di-(tert-butyl)-4-hydroxy-N-(1H-tetrazol-5-yl)-benzamide;
3,5-Dimethyl-4-hydroxy-N-(1-methyl-1H-tetrazol-5-yl)-benzamide;
3,5-Di-(tert-butyl)-4-hydroxy-N-(1-methyl-1H-tetrazol-5-yl)-benzamide;
3,5-Di-(tert-butyl)-4-hydroxy-N-(8-hydroxyquinolin-5-yl)-benzamide;
2-(3,5-Di-(tert-butyl)-4-hydroxy-benzoylamino)-thiazole-4-carboxylic acid ethyl ester;
3,5-Di-(tert-butyl)-4-hydroxy-N-(pyridin-2-yl)- methyl benzamide, and
3,5-Dimethyl-4-hydroxy-N-(pyridine-2-yl) methyl benzamide.

13. The compound of claim 1, wherein when $R_3$ is $CO_2H$ or $CONH_2$, $R_1$ is not H and $R_2$ is selected from the group consisting of ethyl, propyl, butyl, isopropyl, tert-butyl, cyclopentyl, and cyclohexyl.

14. The pharmaceutical composition of claim 9, wherein when $R_3$ is $CO_2H$ or $CONH_2$, $R_1$ not H and $R_2$ is selected from the group consisting of ethyl, propyl, butyl, isopropyl, tert-butyl, cyclopentyl, and cyclohexyl.

* * * * *